(12) United States Patent
Clements

(10) Patent No.: US 11,382,884 B2
(45) Date of Patent: Jul. 12, 2022

(54) METHOD FOR REDUCING LUNG INFECTION

(71) Applicant: Respirion Pharmaceuticals Pty Ltd, Iluka (AU)

(72) Inventor: Barry Clements, Iluka (AU)

(73) Assignee: Respirion Pharmaceuticals PTY LTD, Iluka (CA)

( * ) Notice: Subject to any disclaimer, the term of this patent is extended or adjusted under 35 U.S.C. 154(b) by 114 days.

(21) Appl. No.: 16/615,072

(22) PCT Filed: Jun. 20, 2018

(86) PCT No.: PCT/AU2018/050610
§ 371 (c)(1),
(2) Date: Nov. 19, 2019

(87) PCT Pub. No.: WO2018/232453
PCT Pub. Date: Dec. 27, 2018

(65) Prior Publication Data
US 2020/0108033 A1 Apr. 9, 2020

(30) Foreign Application Priority Data

Jun. 20, 2017 (AU) ............... 2017902364
Mar. 8, 2018 (AU) ............... 2018900765

(51) Int. Cl.
| | |
|---|---|
| *A61K 31/198* | (2006.01) |
| *A61K 31/7036* | (2006.01) |
| *A61K 31/133* | (2006.01) |
| *A61P 31/04* | (2006.01) |
| *A61P 11/00* | (2006.01) |
| *A61P 9/00* | (2006.01) |
| *A61K 9/00* | (2006.01) |

(52) U.S. Cl.
CPC .......... *A61K 31/198* (2013.01); *A61K 9/0073* (2013.01); *A61K 31/133* (2013.01); *A61K 31/7036* (2013.01); *A61P 11/00* (2018.01); *A61P 31/04* (2018.01)

(58) Field of Classification Search
CPC .. A61K 9/0073; A61K 31/133; A61K 31/198; A61K 31/7036; A61K 31/427; A61K 38/12; A61K 45/06; A61K 2300/00; A61P 31/00; A61P 31/04; A61P 11/80
USPC .......................................................... 514/40
See application file for complete search history.

(56) References Cited

U.S. PATENT DOCUMENTS 5,823,178 A 10/1998 Lloyd et al.
2016/0263151 A1* 9/2016 Hassett ................. A61K 45/06

FOREIGN PATENT DOCUMENTS

| WO | WO 2008/137747 A1 * | 11/2008 | ............ A61K 39/12 |
|---|---|---|---|
| WO | WO-2008/137747 A1 | 11/2008 | |
| WO | WO 2011/142677 | 11/2011 | |

OTHER PUBLICATIONS

The Merck Manual, 1992, 16th Ed., pp. 100, 110 and 225).*
Search Report, dated Jul. 16, 2018, WO, PCT/AU2018/050610.
Asmus et al., Pulmonary function response to EDTA, an additive in nebulized bronchodilators, The Journal of Allergy and Clinical Immunology, vol. 107(1):68-72, Jan. 2001.
Beasley et al., Bronchoconstrictor properties of preservatives in ipratropium bromide (Atrovent) nebuliser solution, British Medical Journal (Clinical Research Ed.), vol. 294(6581:1197-8, May 1987.
Brown et al., Edetate Sodium Aerosol in Pseudomonas Lung Infection in Cystic Fibrosis, American Journal of Diseases of Children, vol. 139(8):836-9, Aug. 1985.
Bueno, J., Anti-Biofilm Drug Susceptibility Testing Methods: Looking for New Strategies Against Resistance Mechanism, Journal of Microbial & Biochemical Technology, vol. S3(004):1-9, May 2014.
Clifton et al., The Effect of Lipopolysaccharide Core Oligosaccharide Size on the Electrostatic Binding of Antimicrobial Proteins to Models of the Gram Negative Bacterial Outer Membrane, Langmiur, vol. 32(14):3485-3494, Mar. 2016.
Fajardo et al., Characterization of a novel $Zn^{2+}$-dependent intrinsic imipenemase from Pseudomonas aeruginosa, The Journal of Antimicrobial Chemotherapy, vol. 69(11):2972-8, Nov. 2014.
Gaggar et al., The Role of Matrix Metalloproteinases in Cystic Fibrosis Lung Disease, European Respiratory Journal, vol. 38(3):721-727, 2011.
Garrat et al., Matrix metalloproteinase activation by free neutrophil elastase contributes to bronchiectasis progression in early cystic fibrosis, The European Respiratory Journal, vol. 46(2):384-94, Aug. 2015.
Haley et al., Characterization of biofilm-like structures formed by Pseudomonas aeruginosa in a synthetic mucus medium, BMC Microbiology, vol. 12:181, Aug. 2012.
Hazra et al., Modulation of matrix metalloproteinase activity by EDTA prevents posterior capsular opacification, Molecular Vision, vol. 18:1701-1711, Jun. 2012.
Hassett et al., Chronic Obstructive Pulmonary Disease (COPD): Evaluation Form Clinical, Immunological and Bacterial Pathogenesis Perspective, Journal of Microbiology, vol. 52(3):211-226, Mar. 2014.
Hoffman et al., Aminoglycoside antibiotics induce bacterial biofilm formation, Nature, vol. 436:1171-1175, Aug. 2005.
Hunter et al., Ferrous Iron Is a Significant Component of Bioavailable Iron in Cystic Fibrosis Airways, MBio, vol. 4(4):1-8, Aug. 2013.
Jomova et al, Advances in metal-induced oxidative stress and human disease, Toxicology, vol. 283(2-3):65-87, May 2011.
Jones et al., Subinhibitory Concentration of Kanamycin Induces the Pseudomonas aeruginosa type VI Secretion System, PLOS One, vol. 8(11):e81132, Nov. 2013.

(Continued)

*Primary Examiner* — Ganapathy Krishnan
(74) *Attorney, Agent, or Firm* — Howson & Howson LLP; Colleen Schaller

(57) ABSTRACT

A method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8h.

13 Claims, 19 Drawing Sheets

(56) References Cited

OTHER PUBLICATIONS

Kettle et al., Oxidation Contributes to Low Glutathione in the Airways of Children with Cystic Fibrosis, The European Respiratory Journal, vol. 44(1):122-9, Jul. 2014.

Lebeaux et al., pH-mediated potentiation of aminoglycosides kills bacterial persisters and eradicates in vivo biofilms, Journal Infectious Diseases, vol. 210(9):1357-66, Nov. 2014.

McDaniel et al., A Putative ABC Transporter Permease Is Necessary for Resistance to Acidified Nitrite and EDTA in Pseudomonas aeruginosa under Aerobic and Anaerobic Planktonic and Biofilm Conditions, Frontiers in Microbiology, vol. 7:291, Apr. 2016.

Moradali et al., Pseudomonas Aeruginosa Lifestyle: A Paradigm for Adaptation, Survival, and Persistence, Frontiers in Cellular and Infection Microbiology, Nature Communications, vol. 7:39, Feb. 2017.

Olson et al., Efficient production and processing of elastase and LasA by Pseudomonas aeruginosa require zinc and calcium ions, Journal of Bacteriology, vol. 174(12):4140-7, Jun. 1992.

Orhan et al., Synergy Tests by E Test and Checkerboard Methods of Antimicrobial Combinations against *Brucella melitensis*, Journal Clinical Microbiology, vol. 43(1):140-143, Jan. 2005.

Schultz et al., Airway surface liquid pH is not acidic in children with cystic fibrosis, vol. 8(1):1409, Nov. 2017.

Silva-Filho et al., Pseudomonas aeruginosa infection in patients with cystic fibrosis: scientific evidence regarding clinical impact, diagnosis, and treatment, Journal Brasilerio de Pneumologia, vol. 39(4):495-512, Jun. 2013.

Silvaneson et al., Two-component regulatory systems in Pseudomonas aeruginosa: an intricate network mediating fimbrial and efflux pump gene expression, Molecular Microbiology, vol. 79(5):1353-66, Mar. 2011.

Stewart et al., Antibiotic Resistance of Bacteria in Biofilms, Lancet, vol. 358(9276):135-8, Jul. 2001.

Stites et al., Increased Concentrations of Iron and Isoferritinsin the Lower Respiratory Tract of Patients with Stable Cystic Fibrosis, American Journal of Respiratory and Critical Care Medicine, vol. 160(3):796-801, Nov. 1998.

Vaara, M., Agents that increase the permeability of the outer membrane, Microbiological Reviews, vol. 56(3):395-411, Sep. 1992.

International Search Report and Written Opinion issued in International Patent Application No. PCT/AU2018/050610, dated Jul. 16, 2018.

Andersen et al., 3D Cell Culture in Alginate Hydrogels, Microarrays, Mar. 2015, 4, 133-161; doi:10.3390/microarrays4020133.

Wood et al., The Effect of EDTA and Antibiotics on Pseudomonas Aeruginosa Isolated from Cystic Fibrosis Patients: A New Chemotherapeutic Approach, in Perspectives in Cystic Fibrosis, ed J. M. Sturgess (Toronto, ON: Canadian Cystic Fibrosis Foundation), 1980, 365-369.

* cited by examiner

|  | CaEDTA (mM) | | | | | | | | | |
|---|---|---|---|---|---|---|---|---|---|---|
| Tobramycin (ug/ml) | 40 | 20 | 10 | 5 | 2.5 | 1.25 | 0.625 | 0.31 | 0.15 | 0 |
| 16 | 0.038 | 0.037 | 0.037 | 0.037 | 0.037 | 0.037 | 0.037 | 0.037 | 0.037 | 0.037 |
| 8 | 0.038 | 0.038 | 0.038 | 0.037 | 0.037 | 0.038 | 0.037 | 0.038 | 0.038 | 0.037 |
| 4 | 0.039 | 0.039 | 0.039 | 0.038 | 0.037 | 0.037 | 0.037 | 0.114 | 0.038 | 0.041 |
| 2 | 0.089 | 0.053 | 0.046 | 0.045 | 0.053 | 0.069 | 0.097 | 0.129 | 0.193 | 0.668 |
| 1 | 0.608 | 0.656 | 0.659 | 0.735 | 0.729 | 0.839 | 0.860 | 0.903 | 0.979 | 0.986 |
| 0 | 0.992 | 0.979 | | | | | | | | |

Figure 1A

|  | Buffered EDTA (mM) | | | | | | | | | |
|---|---|---|---|---|---|---|---|---|---|---|
| Tobramycin (ug/ml) | 20 | 10 | 5 | 2.5 | 1.25 | 0.625 | 0.3125 | 0.156 | 0.078 | 0 |
| 16 | 0.038 | 0.037 | 0.037 | 0.037 | 0.037 | 0.038 | 0.038 | 0.037 | 0.038 | 0.037 |
| 8 | 0.040 | 0.038 | 0.038 | 0.037 | 0.038 | 0.038 | 0.038 | 0.038 | 0.038 | 0.038 |
| 4 | 0.040 | 0.039 | 0.039 | 0.038 | 0.038 | 0.038 | 0.038 | 0.039 | 0.038 | 0.043 |
| 2 | 0.040 | 0.039 | 0.048 | 0.040 | 0.045 | 0.073 | 0.172 | 0.210 | 0.275 | 0.763 |
| 1 | 0.042 | 0.044 | 0.389 | 0.762 | 0.842 | 0.901 | 0.941 | 0.979 | 0.995 | |
| 0 | 0.960 | | | | | | | | | |

Figure 1B

|  | CaEDTA (mM) | | | | | | | | | |
|---|---|---|---|---|---|---|---|---|---|---|
| Tobramycin (ug/ml) | 40 | 20 | 10 | 5 | 2.5 | 1.25 | 0.625 | 0.313 | 0.156 | 0 |
| 16 | 0.156 | 0.144 | 0.141 | 0.182 | 0.154 | 0.162 | 0.161 | 0.158 | 0.140 | 0.166 |
| 8 | 0.159 | 0.131 | 0.156 | 0.162 | 0.171 | 0.167 | 0.149 | 0.172 | 0.165 | 0.205 |
| 4 | 0.199 | 0.167 | 0.179 | 0.195 | 0.179 | 0.176 | 0.180 | 0.180 | 0.212 | 0.530 |
| 2 | 0.835 | 0.523 | 0.416 | 0.396 | 0.579 | 0.687 | 1.204 | 1.678 | | |
| 1 | | | | | | | | | | |
| 0 | | | | | | | | | | |

Figure 2A

|  | Buffered EDTA (mM) | | | | | | | | | |
|---|---|---|---|---|---|---|---|---|---|---|
| Tobramycin (ug/ml) | 20 | 10 | 5 | 2.5 | 1.25 | 0.625 | 0.3125 | 0.156 | 0.078 | 0 |
| 16 | 0.171 | 0.174 | 0.153 | 0.154 | 0.165 | 0.149 | 0.139 | 0.169 | 0.163 | 0.172 |
| 8 | 0.136 | 0.150 | 0.150 | 0.141 | 0.183 | 0.131 | 0.126 | 0.139 | 0.151 | 0.175 |
| 4 | 0.140 | 0.156 | 0.158 | 0.120 | 0.162 | 0.141 | 0.143 | 0.165 | 0.186 | 0.225 |
| 2 | 0.128 | 0.240 | 0.274 | 0.212 | 0.228 | 0.313 | 0.277 | 0.336 | 0.396 | 1.727 |
| 1 | 0.167 | 0.276 | 0.294 | 0.345 | 0.457 | 0.644 | 0.769 | 1.110 | 1.571 | |
| 0 | 1.879 | | | 1.990 | 1.987 | 1.505 | 1.511 | 1.721 | 1.552 | 1.882 |

Figure 2B

| Tobramycin (ug/ml) | CaEDTA (mM) | | | | | | | | | |
|---|---|---|---|---|---|---|---|---|---|---|
| | 40 | 20 | 10 | 5 | 2.5 | 1.25 | 0.625 | 0.3 | 0.15 | 0 |
| 16 | 0.039 | 0.039 | 0.039 | 0.039 | 0.039 | 0.039 | 0.039 | 0.038 | 0.039 | 0.039 |
| 8 | 0.047 | 0.043 | 0.042 | 0.042 | 0.042 | 0.042 | 0.042 | 0.043 | 0.041 | 0.044 |
| 4 | 0.123 | 0.111 | 0.108 | 0.112 | 0.119 | 0.131 | 0.152 | 0.151 | 0.182 | 0.181 |
| 2 | 0.516 | 0.686 | 0.664 | 0.665 | 0.676 | 0.797 | 0.816 | 0.871 | 0.852 | 0.905 |
| 1 | 0.895 | 0.662 | 0.597 | 0.637 | 0.705 | 0.765 | 0.795 | 0.822 | 0.871 | |
| 0 | 0.992 | | | 0.881 | 0.906 | 0.925 | 0.944 | 0.987 | | |

Figure 3A

| Tobramycin (ug/ml) | Buffered EDTA (mM) | | | | | | | | | |
|---|---|---|---|---|---|---|---|---|---|---|
| | 40 | 20 | 10 | 5 | 2.5 | 1.25 | 0.625 | 0.3 | 0.15 | 0 |
| 16 | 0.038 | 0.038 | 0.038 | 0.039 | 0.039 | 0.039 | 0.039 | 0.038 | 0.038 | 0.039 |
| 8 | 0.039 | 0.040 | 0.040 | 0.040 | 0.040 | 0.041 | 0.041 | 0.041 | 0.041 | 0.042 |
| 4 | 0.049 | 0.066 | 0.073 | 0.075 | 0.073 | 0.088 | 0.097 | 0.109 | 0.110 | 0.150 |
| 2 | 0.149 | 0.216 | 0.373 | 0.483 | 0.608 | 0.674 | 0.707 | 0.742 | 0.741 | 0.820 |
| 1 | 0.685 | 0.765 | 0.760 | 0.705 | 0.728 | 0.739 | 0.807 | 0.818 | 0.866 | |
| 0 | 0.913 | 0.818 | 0.899 | 0.939 | 0.893 | 0.947 | 0.984 | | | |

Figure 3B

| Tobramycin (ug/ml) | CaEDTA (mM) | | | | | | | | | |
|---|---|---|---|---|---|---|---|---|---|---|
| | 40 | 20 | 10 | 5 | 2.5 | 1.25 | 0.625 | 0.31 | 0.15 | 0 |
| 16 | 0.258 | 0.232 | 0.230 | 0.253 | 0.240 | 0.234 | 0.244 | 0.242 | 0.259 | 0.297 |
| 8 | 0.589 | 0.499 | 0.431 | 0.470 | 0.454 | 0.413 | 0.426 | 0.523 | 0.468 | 0.769 |
| 4 | | 1.956 | 1.730 | 1.962 | | | | | | |
| 2 | | | | | 2.548 | | | | 1.992 | |
| 1 | | | | | 2.456 | | | | | |
| 0 | | | | | | | | | | |

Figure 4A

| Tobramycin (ug/ml) | Buffered EDTA (mM) | | | | | | | | | |
|---|---|---|---|---|---|---|---|---|---|---|
| | 40 | 20 | 10 | 5 | 2.5 | 1.25 | 0.625 | 0.31 | 0.15 | 0 |
| 16 | 0.207 | 0.197 | 0.211 | 0.213 | 0.221 | 0.219 | 0.214 | 0.226 | 0.231 | 0.259 |
| 8 | 0.245 | 0.309 | 0.320 | 0.317 | 0.345 | 0.351 | 0.359 | 0.424 | 0.391 | 0.500 |
| 4 | 0.533 | 0.957 | 1.137 | 1.069 | 1.652 | 1.858 | 1.935 | | | |
| 2 | | | | | | | | | | |
| 1 | | | | | | | | | | |
| 0 | | | | | | | | | | |

Figure 4B

|                      | Buffered EDTA (mM) |       |       |       |       |       |        |       |       |       |
|----------------------|--------------------|-------|-------|-------|-------|-------|--------|-------|-------|-------|
| Methicillin (ug/ml)  | 20                 | 10    | 5     | 2.5   | 1.25  | 0.625 | 0.3125 | 0.156 | 0.078 | 0     |
| 1024                 | 0.102              | 0.108 | 0.093 | 0.092 | 0.122 | 0.106 | 0.102  | 0.111 | 0.108 | 0.137 |
| 512                  | 0.120              | 0.109 | 0.158 | 0.096 | 0.101 | 0.188 | 0.445  | 0.108 | 0.107 | 0.519 |
| 256                  | 0.287              | 0.344 | 0.343 | 0.377 | 0.360 | 0.410 | 0.361  | 0.426 | 0.440 | 0.330 |
| 128                  | 0.914              | 0.857 | 0.785 | 0.720 | 0.804 | 0.780 | 0.794  | 0.841 | 0.841 | 1.090 |
| 64                   | 0.958              | 0.909 | 0.966 | 0.978 | 0.991 | 1.000 | 1.004  | 1.002 | 1.026 | 1.095 |
| 0                    | 1.022              | 1.023 | 1.034 | 1.026 | 1.035 | 1.049 | 1.046  | 1.046 | 1.059 | 1.076 |

Figure 7

|                       | CaEDTA (mM) |       |       |       |       |       |       |       |       |       |
|-----------------------|-------------|-------|-------|-------|-------|-------|-------|-------|-------|-------|
| Carbenicillin (ug/ml) | 20          | 10    | 5     | 2.5   | 1.25  | 0.625 | 0.31  | 0.155 | 0.075 | 0     |
| 250                   | 0.037       | 0.037 | 0.037 | 0.038 | 0.038 | 0.038 | 0.038 | 0.037 | 0.038 | 0.041 |
| 125                   | 0.038       | 0.038 | 0.039 | 0.040 | 0.041 | 0.041 | 0.042 | 0.042 | 0.043 | 0.093 |
| 62.5                  | 0.046       | 0.041 | 0.044 | 0.048 | 0.049 | 0.052 | 0.056 | 0.064 | 0.070 | 0.213 |
| 31.25                 | 0.050       | 0.053 | 0.058 | 0.063 | 0.070 | 0.073 | 0.080 | 0.088 | 0.101 | 0.291 |
| 15.5                  | 0.071       | 0.075 | 0.080 | 0.086 | 0.095 | 0.103 | 0.101 | 0.111 | 0.126 | 0.310 |
| 0                     | 0.124       | 0.155 | 0.157 | 0.162 | 0.172 | 0.205 | 0.256 | 0.233 | 0.247 | 0.347 |

Figure 8A

|                       | CaEDTA (mM) |       |       |       |       |       |       |       |       |       |
|-----------------------|-------------|-------|-------|-------|-------|-------|-------|-------|-------|-------|
| Carbenicillin (ug/ml) | 20          | 10    | 5     | 2.5   | 1.25  | 0.625 | 0.31  | 0.155 | 0.075 | 0     |
| 250                   | 0.202       | 0.279 | 0.258 | 0.325 | 0.283 | 0.362 | 0.315 | 0.299 | 0.363 | 0.744 |
| 125                   | 0.137       | 0.209 | 0.306 | 0.468 | 0.544 | 0.663 | 0.695 | 0.592 | 0.989 | 3.167 |
| 62.5                  | 0.311       | 0.345 | 0.636 | 1.010 | 1.241 | 1.563 | 1.548 | 2.232 | 2.488 | 4.651 |
| 31.25                 | 1.018       | 1.035 | 1.209 | 1.724 | 1.980 | 2.056 | 2.228 | 2.399 | 2.550 | 3.935 |
| 15.5                  | 2.026       | 2.093 | 1.639 | 2.051 | 1.930 | 2.226 | 2.626 | 3.068 | 3.251 | 3.241 |
| 0                     | 2.386       | 2.652 | 2.373 | 2.547 | 2.938 | 2.702 | 2.741 | 2.258 | 3.107 | 2.658 |

Figure 8B

| Tobramycin (ug/ml) | EGTA (mM) | | | | | | | | | |
|---|---|---|---|---|---|---|---|---|---|---|
| | 40 | 20 | 10 | 5 | 2.5 | 1.25 | 0.625 | 0.31 | 0.15 | 0 |
| 16 | 0.038 | 0.038 | 0.038 | 0.038 | 0.038 | 0.038 | 0.038 | 0.038 | 0.038 | 0.038 |
| 8 | 0.039 | 0.039 | 0.040 | 0.040 | 0.040 | 0.068 | 0.041 | 0.042 | 0.042 | 0.042 |
| 4 | 0.145 | 0.238 | 0.255 | 0.281 | 0.289 | 0.314 | 0.386 | 0.343 | 0.327 | 0.135 |
| 2 | 0.406 | 0.472 | 0.663 | 0.697 | 0.751 | 0.770 | 0.769 | 0.734 | 0.858 | 0.677 |
| 1 | 0.420 | 0.467 | 0.889 | 0.812 | 0.824 | 0.789 | 0.803 | 0.797 | 0.666 | 0.900 |
| 0 | 0.446 | 0.520 | 0.632 | 0.790 | 0.866 | 0.889 | 0.804 | 0.932 | 0.864 | 0.986 |

| Tobramycin (ug/ml) | DTPA (mM) | | | | | | | | | |
|---|---|---|---|---|---|---|---|---|---|---|
| | 3.1 | 1.6 | 0.78 | 0.39 | 0.19 | 0.10 | 0.05 | 0.02 | 0.01 | 0 |
| 8 | 0.094 | 0.099 | 0.078 | 0.052 | 0.040 | 0.039 | 0.039 | 0.044 | 0.038 | 0.038 |
| 4 | 0.066 | 0.079 | 0.073 | 0.048 | 0.044 | 0.043 | 0.043 | 0.043 | 0.042 | 0.041 |
| 2 | 0.060 | 0.086 | 0.091 | 0.069 | 0.065 | 0.071 | 0.067 | 0.063 | 0.096 | 0.450 |
| 1 | 0.060 | 0.092 | 0.113 | 0.131 | 0.137 | 0.214 | 0.399 | 0.510 | 0.600 | 0.687 |
| 0.5 | 0.059 | 0.090 | 0.118 | 0.207 | 0.452 | 0.618 | 0.915 | 0.874 | 0.885 | 0.961 |
| 0 | 0.061 | 0.094 | 0.137 | 0.339 | 0.663 | 0.894 | 0.807 | 0.806 | 0.861 | 0.923 |
Figure 14A
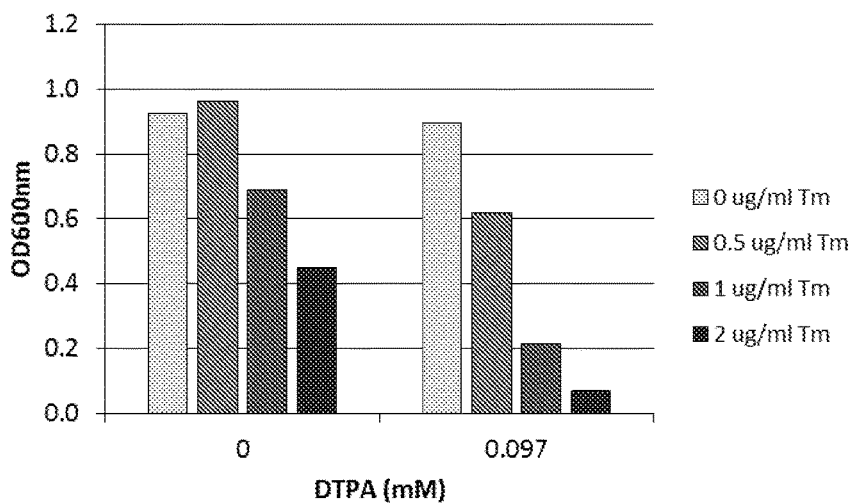
Figure 14B
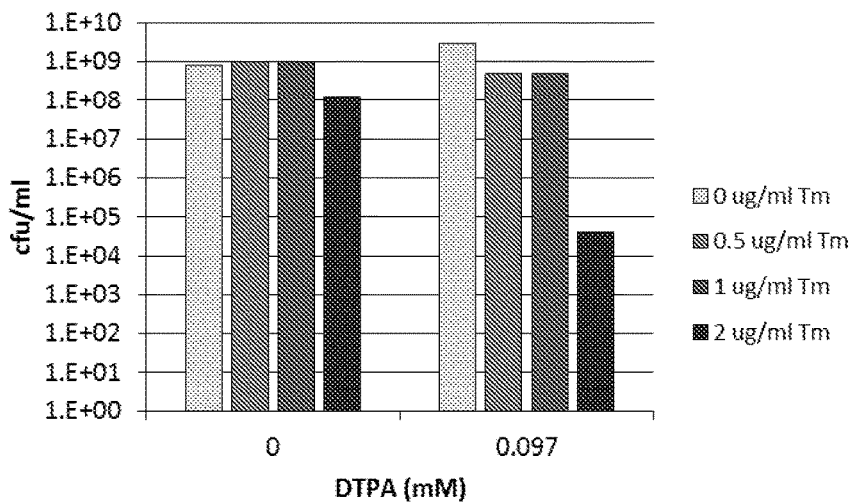
Figure 14C

| Tobramycin (ug/ml) | Buffered EDTA (mM) | | | | | | | | | |
|---|---|---|---|---|---|---|---|---|---|---|
| | 20 | 10 | 5 | 2.5 | 1.25 | 0.625 | 0.3125 | 0.156 | 0.078 | 0 |
| 32 | 0.046 | 0.055 | 0.084 | 0.092 | 0.107 | 0.119 | 0.123 | 0.146 | 0.188 | 0.321 |
| 16 | 0.101 | 0.114 | 0.138 | 0.144 | 0.163 | 0.189 | 0.206 | 0.255 | 0.314 | 0.535 |
| 8 | 0.147 | 0.149 | 0.204 | 0.237 | 0.264 | 0.311 | 0.346 | 0.407 | 0.457 | 0.640 |
| 4 | 0.169 | 0.189 | 0.255 | 0.274 | 0.320 | 0.358 | 0.413 | 0.479 | 0.510 | 0.655 |
| 2 | 0.227 | 0.204 | 0.250 | 0.274 | 0.332 | 0.369 | 0.424 | 0.495 | 0.522 | 0.657 |
| 0 | 0.247 | 0.236 | 0.251 | 0.267 | 0.312 | 0.349 | 0.407 | 0.467 | 0.516 | 0.663 |

| Ciprofloxacin (ug/ml) | Buffered CaEDTA (mM) | | | | | | | | | |
|---|---|---|---|---|---|---|---|---|---|---|
| | 20 | 10 | 5 | 2.5 | 1.25 | 0.625 | 0.31 | 0.15 | 0.075 | 0 |
| 8 | 0.051 | 0.049 | 0.047 | 0.048 | 0.048 | 0.048 | 0.048 | 0.048 | 0.048 | 0.049 |
| 4 | 0.084 | 0.074 | 0.072 | 0.069 | 0.071 | 0.076 | 0.070 | 0.078 | 0.103 | 0.127 |
| 2 | 0.258 | 0.321 | 0.318 | 0.328 | 0.335 | 0.381 | 0.429 | 0.442 | 0.469 | 0.623 |
| 1 | 0.364 | 0.385 | 0.395 | 0.397 | 0.410 | 0.436 | 0.467 | 0.511 | 0.522 | 0.735 |
| 0.5 | 0.468 | 0.477 | 0.468 | 0.484 | 0.507 | 0.528 | 0.565 | 0.615 | 0.640 | 0.865 |
| 0 | 0.580 | 0.573 | 0.578 | 0.609 | 0.616 | 0.684 | 0.762 | 0.816 | 0.834 | 1.030 |

Figure 16

| Colistin (ug/ml) | CaEDTA (mM) | | | | | | | | | |
|---|---|---|---|---|---|---|---|---|---|---|
| | 20 | 10 | 5 | 2.5 | 1.25 | 0.63 | 0.31 | 0.156 | 0.078 | 0 |
| 64 | 0.038 | 0.038 | 0.038 | 0.038 | 0.038 | 0.040 | 0.045 | 0.120 | 0.442 | 0.561 |
| 32 | 0.038 | 0.038 | 0.038 | 0.040 | 0.039 | 0.080 | 0.366 | 0.540 | 0.603 | 0.349 |
| 16 | 0.038 | 0.039 | 0.073 | 0.403 | 0.475 | 0.503 | 0.492 | 0.496 | 0.637 | 0.679 |
| 8 | 0.525 | 0.496 | 0.497 | 0.640 | 0.569 | 0.635 | 0.690 | 0.801 | 0.844 | 0.860 |
| 4 | 0.602 | 0.583 | 0.586 | 0.649 | 0.737 | 0.834 | 0.827 | 0.906 | 0.935 | 0.957 |
| 0 | 0.948 | 0.936 | 0.908 | 0.879 | 0.870 | 0.871 | 0.896 | 0.925 | 0.952 | 1.006 |

Figure 17A

| Colistin (ug/ml) | CaEDTA (mM) | | | | | | | | | |
|---|---|---|---|---|---|---|---|---|---|---|
| | 20 | 10 | 5 | 2.5 | 1.25 | 0.63 | 0.31 | 0.156 | 0.078 | 0 |
| 64 | 0.148 | 0.220 | 0.158 | 0.146 | 0.171 | 0.138 | 0.145 | 0.285 | 0.190 | 0.226 |
| 32 | 0.131 | 0.150 | 0.116 | 0.139 | 0.120 | 0.206 | 0.214 | 0.348 | 0.386 | 1.096 |
| 16 | 0.142 | 0.161 | 0.225 | 0.217 | 0.390 | 0.604 | 0.635 | 1.004 | 2.152 | 1.582 |
| 8 | 0.379 | 0.457 | 0.569 | 1.100 | 1.024 | 1.253 | 1.698 | 2.419 | 2.441 | 2.485 |
| 4 | 0.506 | 0.569 | 0.746 | 0.878 | 1.667 | 2.378 | 2.556 | 3.334 | 3.690 | 2.916 |
| 0 | 2.109 | 2.717 | 2.906 | 3.613 | 3.205 | 3.214 | 3.519 | 3.281 | 3.787 | 3.084 |

Figure 17B

| Tetracycline (ug/ml) | Buffered EDTA (mM) | | | | | | | | | |
|---|---|---|---|---|---|---|---|---|---|---|
| | 20 | 10 | 5 | 2.5 | 1.25 | 0.625 | 0.3125 | 0.156 | 0.078 | 0 |
| 64 | 0.080 | 0.086 | 0.118 | 0.092 | 0.092 | 0.098 | 0.100 | 0.105 | 0.104 | 0.100 |
| 32 | 0.080 | 0.084 | 0.089 | 0.089 | 0.105 | 0.093 | 0.096 | 0.099 | 0.096 | 0.096 |
| 16 | 0.077 | 0.083 | 0.086 | 0.090 | 0.089 | 0.091 | 0.093 | 0.099 | 0.097 | 0.093 |
| 8 | 0.078 | 0.082 | 0.426 | 0.466 | 0.392 | 0.630 | 0.409 | 0.671 | 0.616 | 0.540 |
| 4 | 0.241 | 0.324 | 0.770 | 0.727 | 0.776 | 0.520 | 0.740 | 0.701 | 0.643 | 0.505 |
| 0 | 0.752 | 0.663 | 0.865 | 0.619 | 0.811 | 0.595 | 0.633 | 0.764 | 0.608 | 0.712 |

Figure 18

| Vancomycin (ug/ml) | Buffered EDTA (mM) | | | | | | | | | |
|---|---|---|---|---|---|---|---|---|---|---|
| | 20 | 10 | 5 | 2.5 | 1.25 | 0.625 | 0.3125 | 0.156 | 0.078 | 0 |
| 0.25 | 0.044 | 0.044 | 0.045 | 0.045 | 0.045 | 0.045 | 0.045 | 0.044 | 0.045 | 0.046 |
| 0.125 | 0.044 | 0.155 | 0.249 | 0.250 | 0.299 | 0.289 | 0.063 | 0.043 | 0.044 | 0.044 |
| 0.0625 | 0.193 | 0.234 | 0.308 | 0.319 | 0.401 | 0.437 | 0.443 | 0.464 | 0.399 | 0.446 |
| 0.0313 | 0.253 | 0.308 | 0.329 | 0.330 | 0.385 | 0.376 | 0.405 | 0.445 | 0.461 | 0.461 |
| 0.0156 | 0.256 | 0.310 | 0.314 | 0.317 | 0.329 | 0.336 | 0.387 | 0.403 | 0.417 | 0.418 |
| 0 | 0.256 | 0.295 | 0.309 | 0.316 | 0.335 | 0.371 | 0.375 | 0.401 | 0.417 | 0.435 |

Figure 19

METHOD FOR REDUCING LUNG INFECTION

CROSS-REFERENCE TO RELATED APPLICATIONS

This is a National Stage Entry under 35 U.S.C. 371 of International Patent Application No. PCT/AU2018/050610, filed Jun. 20, 2018, which claims priority to Australian Patent Application No. 2017902364, filed Jun. 20, 2017, and Australian Patent Application No. 2018900765, filed Mar. 8, 2018. These applications are incorporated by reference herein.

TECHNICAL FIELD

The present invention relates to a method of treating or preventing bacterial infection in the lung of a subject by administering a high concentration of an inhaled chelating agent in combination with an inhaled antibiotic, and formulations to use in the method.

BACKGROUND ART

Eradication of microbial infections can be challenging, especially when host defences are compromised. In addition, many microbes form highly organised structures called biofilms in which they are protected from immune cells and antibiotic killing via several mechanisms. These mechanisms include reduced antibiotic penetration, low metabolic activity, physiological adaptation, antibiotic-degrading enzymes, and selection for genetically resistant variants (Stewart & Costerton Lancet. 2001 358(9276):135-138).

*Pseudomonas aeruginosa* is an example of a Gram-negative bacterium that causes acute and chronic infections in compromised hosts. It is commonly found in intensive care units and has strong biofilm-forming capabilities, which are a well-known obstacle for antibiotic intervention. Diseases that involve *P. aerugionosa* infection include cystic fibrosis (CF), ventilator-associated pneumonia (VAP), and chronic obstructive pulmonary disease (COPD) (Moradali et al. *Front Cell Infect Microbiol.* 2017 7:39; Hassett et al. *J Microbiol.* 2014 52(3):211-226).

Once organisms such as *P. aerugionosa* become established in the CF respiratory tract, successful eradication is impossible due to issues that include the CF lung environment and bacterial resistance mechanisms, e.g. biofilm formation and antibiotic-neutralizing enzymes. *P. aeruginosa* infections eventually become chronic, the infecting strains become increasingly resistant to antimicrobials, and persistent inflammation leads to progressively reduced lung function (Hassett et al. *J Microbiol.* 2014 52(3):211-226). Despite improved treatments, existing drugs have limited efficacy and patients eventually require transplant surgery or die from respiratory failure.

There is a need for methods to treat or prevent infection in the lung; or at least a method for complementing the previously known treatment methods.

The present invention seeks to provide an improved or alternative method for treating or preventing infection in the lung, by administering at least 37.5 mg/day of an inhaled chelating agent in combination with an antibiotic.

The preceding discussion of the background art is intended to facilitate an understanding of the present invention only. The discussion is not an acknowledgment or admission that any of the material referred to is or was part of the common general knowledge as at the priority date of the application.

SUMMARY OF INVENTION

The present invention provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h.

Preferably each of the chelating agent and antibiotic is administered in one to four doses per day.

Preferably from 37.5 mg/day to 1,200 mg/day of chelating agent is administered. Preferably, at least 50 mg/day of chelating agent is administered. The chelating agent may be administered between one and four times daily, up to a total daily dose of about 1,200 mg/day. Preferably, the chelating agent and/or antibiotic are administered over a period of no more than 1 h. Preferably the chelating agent is CaEDTA.

Preferably at least 10 mg/day of the antibiotic is administered, or between 10 mg/day and 1,250 mg/day antibiotic is administered. The antibiotic may be administered between one and four times daily, up to a total daily dose of about 1,250 mg/day, preferably 1,000 mg/day. Preferably the antibiotic is tobramycin.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment reduces inflammation.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment or prevention of infection is associated with or results in a decrease or reduction in MMP activity.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment or prevention of infection is associated with or results in a decrease or reduction in the production of hydroxyl radicals.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment or prevention of infection results in an increase in forced expiratory volume (FEV).

An inhalable dosage form containing an inhalable chelating agent, for use for the treatment of infection, in combination with an inhalable antibiotic, each in one or more doses, wherein at least 37.5 mg/day of the inhaled chelating agent is delivered, wherein the or each dose of the chelating agent and/or antibiotic is administered over a period of no more than 8 h.

An inhalable dosage form containing an inhalable antibiotic, for use for the treatment of infection, in combination with an inhalable chelating agent, each in one or more doses, wherein at least 37.5 mg/day of the inhaled chelating agent is delivered, wherein the or each dose of the chelating agent and/or antibiotic is administered over a period of no more than 8 h.

An inhalable dosage form containing an inhalable chelating agent and an inhalable antibiotic, for use for the treatment of infection, each in one or more doses, wherein at least 37.5 mg/day of the inhaled chelating agent is delivered, wherein the or each dose of the chelating agent and/or antibiotic is administered over a period of no more than 8 h.

The present invention provides a kit for treating or preventing a bacterial infection in the lung of a subject containing (i) at least 37.5 mg of an inhaled chelating agent; and (ii) instructions for use, wherein the instructions provide that at least 37.5 mg/day of the inhaled chelating agent is delivered with an inhaled antibiotic, wherein the or each dose of the chelating agent and/or antibiotic is administered over a period of no more than 8 h.

The present invention provides a kit for treating or preventing a bacterial infection in the lung of a subject containing (i) an inhalable antibiotic; and (ii) instructions for use, wherein the instructions provide that the antibiotic is delivered with at least 37.5 mg/day of an inhaled chelating agent is delivered, wherein the or each dose of the chelating agent and/or antibiotic is administered over a period of no more than 8 h.

The present invention provides a kit for treating or preventing a bacterial infection in the lung of a subject containing (i) at least 37.5 mg of an inhaled chelating agent and an inhalable antibiotic; and (ii) instructions for use, wherein the instructions provide that at least 37.5 mg/day of the inhaled chelating agent is delivered, wherein the or each dose of the chelating agent and/or antibiotic is administered over a period of no more than 8 h.

The present invention provides for the use of an inhaled chelating agent for the manufacture of a medicament for the treatment of infection, wherein the inhaled chelating agent will be used in combination with an inhaled antibiotic, wherein at least 37.5 mg/day of the inhaled chelating agent is delivered, wherein the or each dose of the chelating agent and/or antibiotic is administered over a period of no more than 8 h.

The present invention provides for the use of an inhaled antibiotic for the manufacture of a medicament for the treatment of infection, wherein the inhaled antibiotic will be used in combination with an inhaled chelating agent, wherein at least 37.5 mg/day of the inhaled chelating agent is delivered, wherein the or each dose of the chelating agent and/or antibiotic is administered over a period of no more than 8 h.

The present invention provides for the use of an inhaled chelating agent and an inhaled antibiotic for the manufacture of a medicament for the treatment of infection, wherein at least 37.5 mg/day of the inhaled chelating agent is delivered, wherein the or each dose of the chelating agent and/or antibiotic is administered over a period of no more than 8 h.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIGS. 1-6 demonstrate the synergistic effects of tobramycin and CaEDTA or buffered CaEDTA as indicated against *P. aeruginosa* WACC91.

FIG. 1: Checkerboard, planktonic growth (OD600 nm) under aerobic conditions. Data show that there is a synergistic effect between tobramycin and CaEDTA (FIG. 1A) and between tobramycin and tris-buffered CaEDTA (FIG. 1B).

FIG. 2: Checkerboard, biofilm growth (CV staining) under aerobic conditions. Data show a synergistic effect between tobramycin and CaEDTA (FIG. 2A) and this is further enhanced with tris-buffered CaEDTA (FIG. 2B).

FIG. 3: Checkerboard, planktonic growth (OD600 nm) under anaerobic conditions. Data show that there is a synergistic effect between tobramycin and CaEDTA (FIG. 3A) and between tobramycin and tris-buffered CaEDTA (FIG. 3B).

FIG. 4: Checkerboard, biofilms under anaerobic conditions. Data show that there is a synergistic effect between tobramycin and CaEDTA (FIG. 4A) and between tobramycin and tris-buffered CaEDTA (FIG. 4B).

FIG. 5: The effect of CaEDTA and buffered CaEDTA on planktonic cells and biofilms under aerobic and anaerobic conditions. Concentrations were 4 ug/ml tobramycin, 6.25 mM CaEDTA and 12.5 mM Tris buffer as indicated.

FIG. 6 shows the synergistic effect of submicron particles of CaEDTA and tobramycin measured by the metabolism of *P. aeruginosa* biofilms in vitro. *P. aeruginosa* biofilms were grown in 96-well microtiter plates and exposed to aerosolised antibiotic and EDTA particles. FIG. 6A: CaEDTA substantially enhances killing at tobramycin concentrations<1 mg/ml. FIG. 6B: The synergistic effect does not depend on the mode of delivery (solution or dry powder).

FIGS. 7-12 demonstrate that CaEDTA enhances the efficacy of a variety of antibiotics against *P. aeruginosa.*

FIG. 7: Checkerboard, *P. aeruginosa* WACC91 planktonic cells vs Methicillin and CaEDTA.

FIG. 8: Checkerboard, *P. aeruginosa* 001-11R (CF clinical strain) planktonic cells (FIG. 8A) and biofilms (FIG. 8B) vs Carbenicillin and CaEDTA.

FIG. 9: *P. aeruginosa* WACC91 planktonic cells vs tetracycline and buffered CaEDTA measured by OD600 nm (FIG. 9A) and colony forming units, CFU/ml (FIG. 9B).

FIG. 10: *P. aeruginosa* WACC91 vs aztreonam (Azactam) and buffered CaEDTA measured by OD600 nm (FIG. 10A) and CFU/ml (FIG. 10B).

FIG. 11: *P. aeruginosa* WACC91 vs erythromycin and buffered CaEDTA measured by OD600 nm (FIG. 11A) and CFU/ml (FIG. 11B).

FIG. 12: *P. aeruginosa* WACC91 planktonic cells vs colistin and buffered CaEDTA as indicated.

FIGS. 13-14 demonstrate that other chelators also enhance the efficacy of antibiotics.

FIG. 13: Checkerboard, *P. aeruginosa* WACC91 planktonic cells vs tobramycin and ethylene glycol tetraacetic acid (EGTA).

FIG. 14 shows synergy between tobramycin and diethylenetriaminepentaacetic acid (DTPA). FIG. 14A: Checkerboard; FIG. 14B-C OD600 nm and colony counts for selected concentrations of antibiotic and chelator as indicated.

FIGS. 15-21 demonstrate that buffered CaEDTA enhances the efficacy a variety of clinically relevant of antibiotics against different bacterial species, both gram positive and gram negative.

FIG. 16: Checkerboard, *B. cepacia* planktonic cells vs ciprofloxacin and CaEDTA.

FIG. 17: Checkerboard, *Klebsiella pneumoniae* planktonic cells (FIG. 17A) and biofilms (FIG. 17B) vs colistin and CaEDTA.

FIG. 18: Checkerboard, *Streptococcus pyogenes* planktonic cells vs tetracycline and CaEDTA.

FIG. 19: Checkerboard, *Staphylococcus aureus* MRSA planktonic cells vs vancomycin and CaEDTA.

FIG. 20: *S. aureus* MSSA planktonic cells vs ciprofloxacin and CaEDTA as indicated.

FIG. 21: *S. aureus* MRSA planktonic cells vs Ciprofloxacin and CaEDTA as indicated. FIG. 21A: OD600 nm; FIG. 21B: CFU/ml.

FIG. 22: Time-kill assay of *P. aeruginosa* ATCC27853 and ceftazidime (128 ug/ml) with or without buffered CaEDTA (20 mM).

FIG. 23: Time-kill assay of *B. cepacia* ATCC25416 and meropenem (32 ug/ml) with or without buffered CaEDTA (20 mM).

FIG. 24 shows submicron particles of CaEDTA kill *P. aeruginosa* biofilms and act synergistically with tobramycin in vitro. *P. aeruginosa* biofilms were grown in hanging drops of CF mucus and treated with aerosolised EDTA particles and/or tobramycin. The final concentration of tobramycin in the droplets was 325 µg/ml.

FIG. 25 shows that treatment of CF subjects with buffered CaEDTA in addition to tobramycin reduces the bacterial load in CF lungs faster than antibiotic treatment alone. CF subjects were treated with nebulised CaEDTA (EDTA) or saline (placebo), and the bacterial load in expectorated mucus was monitored (colony forming units per gram mucus).

FIG. 26 shows the mean change in FEV1 (% points) in patients treated with CaEDTA or placebo from the start of treatment through to 10 weeks (4 weeks after treatment).

FIG. 27 shows the relationship between FEV1 improvement (0-2 weeks) and body weight.

FIG. 28 shows the EDTA concentration achieved in the sputum of three CF subjects 5 minutes and two hours after treatment with 75 mg nebulised CaEDTA.

DESCRIPTION OF INVENTION

Detailed Description of the Invention

Method of Treatment or Prevention

Figure 5:
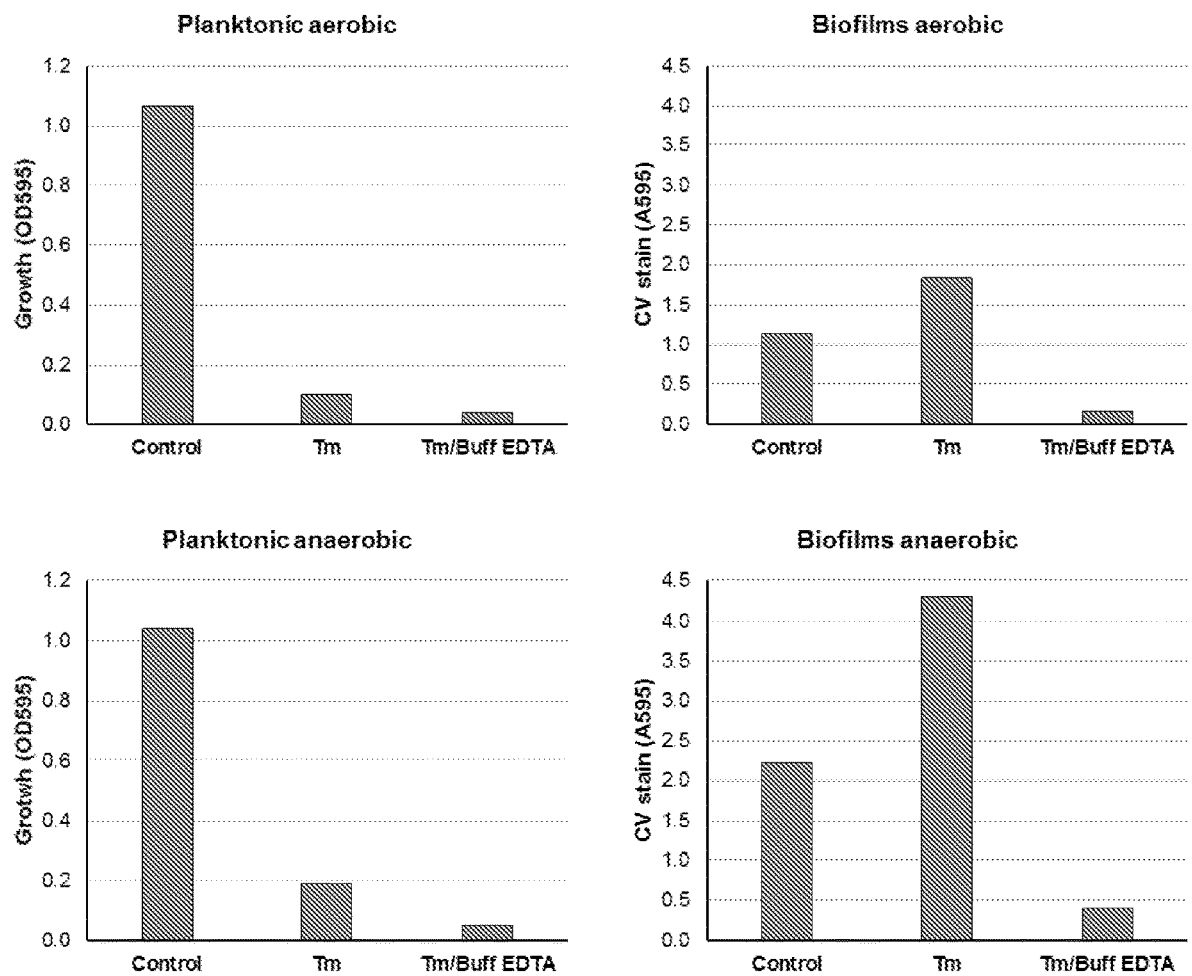

The present invention provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h.

Preferably the subject is an animal, preferably a mammal, most preferably a human.

It has previously been shown that inhaled EDTA alone does not treat bacterial infections (Brown et al. (*Am J Dis Child*. 1985 139(8):836-9); Hassett (*Front Microbiol*. 2016 7:291)). Brown et al. (1985) treated ten CF children chronically infected with *P. aeruginosa* with nebulised sodium EDTA and oral tetracycline for three months and observed no change in lung function or infection status. Others have reported that EDTA causes concentration-dependent bronchoconstriction (Beasley et al. (*Br Med J* (*Clin Res Ed*). 1987 294(6581):1197-8)); and that EDTA has no effect on FEV1 (Asmus et al. (*J Allergy Clin Immunol*. 2001 107(1): 68-72)). Therefore, there would be no reason to believe that a high dose of an inhaled chelating agent would have any positive effect on subjects such as those with cystic fibrosis (CF), asthma, chronic obstructive pulmonary disease (COPD) or other conditions of the lung that cause or are associated with infection and inflammation. However, the present invention has surprisingly found that a certain dose of an inhaled chelating agent in combination with an antibiotic can treat or prevent lung infection and inflammation.

It is a commonly held belief that the CF lung environment is acidic. However, it has been recently shown that the CF lung has the same pH as normal lungs (Schultz et al. "Airway surface liquid pH in children with cystic fibrosis". Nature Communications (8:1409(2017))). Existing technology using acidified nitrite, such as that discussed in US20160263151, is therefore unlikely to work clinically in CF as the formulation does not remain acidified but immediately returns to the normal lung pH of 7.4.

While the acidity of the CF lung is normal, iron levels have been found to be strikingly different from normal lungs. Stites et al. (*Am J Respir Crit Care Med*. 1999 160(3):796-80) showed that iron levels are greatly elevated in the lungs of CF patients, as well as in the lungs of smokers, compared to healthy individuals. It has also been shown that most of this iron is in the ferrous form, Fe(II), and significantly correlates with disease severity (Hunter et al., *MBio*. 2013 4(4):1-8). Ferrous iron can participate in the Fenton reaction to generate highly reactive oxygen radicals that can severely damage tissues and DNA (Jomova et al. Toxicology. 2011 283(2-3):65-87; MacNee, *Eur J Pharmacol*. 2001 429(1-3):195-207).

Without wishing to be bound by theory, it is believed that the method of the present invention reduces infection by in the lungs by depriving the bacteria of essential ions such as iron and zinc. This can happen on a number of levels:
  (i) iron is essential for bacterial growth and survival—this is especially true in the case of biofilm formation, where iron removal leads to bacterial starvation and death;
  (ii) biofilm cells are surrounded by a hydrated polymeric matrix that consists of negatively charged polysaccharides and DNA held together by positively charged metal ions—cation removal causes the biofilms to disperse, thereby making individual bacterial accessible to antibiotics and immune cells;
  (iii) the outer membrane of *P. aeruginosa* and other Gram-negative bacteria consists of negatively charged lipopolysaccharides that are bridged by divalent cations (Clifton et al. *Langmuir* 2015, 31:404-412.)—removal of cations increases outer membrane permeability and antibiotic susceptibility, and this effect is particularly striking in *Pseudomonas* spp. (Vaara, M. *Microbiol Rev* 1992, 56:395-411.); and/or (iv) the key to *P. aeruginosa* survival in the host is the production of secreted virulence factors, several of which depend on metal ions for their function—examples of these are elastase (Zn-dependent, Olson and Ohman, *J Bacteriol* 1992, 174:4140-4147) and β-lactamase (Zn-dependent, Fajardo et al. *J Antimicrob Chemother* 2014, 69:2972-2978).

Inhalation is a localized administration method and can therefore be more effective in reaching the target area, i.e., the lung, and providing a high and localized concentration of the inhaled chelating agent and the antibiotic. Inhalation avoids undesired side effects due to systemic exposure of the actives and reduces the risk of antibiotic resistance.

The chelating agent and the antibiotic may be delivered in one single dosage form, or two separate dosage forms. If the dosage forms are separate, the dosages may be taken together (simultaneously), or one after the other. There may be a temporal separation between delivery of the dosage forms of the two actives of seconds, minutes, hours or days.

The compositions of the present invention may be delivered by puffer (pressurised metered dose inhaler, dry powder inhaler) or by nebuliser. The compositions may be provided in one device (i.e. both the chelating agent and the antibiotic in one device), or the two actives may be delivered from two different devices. For example, the two actives may be delivered by two separate puffers, two separate nebulisers, or a puffer and a nebuliser, with one active in ach device.

The method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h may be provided in the absence of acidified nitrite.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment or prevention of infection results in an increase in FEV.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment or prevention of infection results from the removal or reduction of bacterially produced biofilm in the lungs by the presence of the chelating agent.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment or prevention of infection results from an increase in bacterial outer membrane permeability due to the presence of the chelating agent.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment or prevention of infection results from a reduction in bacterial virulence factors by chelation of metal ions by the chelating agent.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment or prevention of inflammation is associated with a decrease in MMP activity. It is known that matrix metalloproteinases (MMPs) cause lung damage (Garratt et al., *Eur Respir J.* 2015 46(2):384-94) and that MMP activity is $Zn^{2+}$ dependent (Hazra et al. Molecular Vision 2012; 18:1701-1711). However, previous attempts to target MMPs in lungs have been unsuccessful. The present invention uses an inhaled chelating agent to chelate zinc in the lungs, thus reducing MMP induced lung damage and treating or preventing inflammation.

The present invention further provides a method of treating or preventing a bacterial infection in the lung of a subject by administering an inhaled antibiotic, and at least 37.5 mg/day of an inhaled chelating agent, each in one or more doses, wherein the or each dose of the chelating agent and/or antibiotic is administered over a period of no more than 8 h wherein the treatment or prevention of inflammation is associated with a decrease in the production of hydroxyl radicals. Iron is a key factor in lung damage (Stites et al. (Am J Respir Crit Care Med. 1999 160(3):796-80)) as Fe(II) catalyses the formation of hydroxyl radicals. Fe(II) is abundant in the CF lungs and significantly correlates with disease severity (Hunter et al. *MBio.* 2013 4(4):1-8), but antioxidant trials have so far failed to produce significant improvement in lung function. The present invention uses an inhaled chelating agent to chelate iron in the lungs, thus reducing hydroxyl radical induced lung damage and treating or preventing inflammation.

Preferably, the chelating agent is an iron chelating agent or a zinc chelating agent. More preferably, the chelating agent is a chelator of both iron and zinc (an iron/zinc chelator). Alternatively, the chelating agent may be a mixture of two or more chelating agents, for example a mixture of an iron chelating agent and a zinc chelating agent, or an iron/zinc chelating agent and a zinc chelating agent, or an iron chelating agent and an iron/zinc chelating agent.

The chelating agent is preferably selected from the group consisting of citric acid, phosphates, the di-, tri- and tetra-sodium salts of ethylene diamine tetraacetic acid (EDTA), the calcium salts of EDTA, ethylene glycol-bis-(b-amino-ethylether)-N,N,N',N'-tetraacetic acid (EGTA); 1,2-bis(2-aminophenoxy)ethane-N,N,N',N'-tetraacetic acid (BAPTA); ethylene-N,N'-diglycine (EDDA); 2,2'-(ethylendiimino)-dibutyric acid (EBDA); lauroyl EDTA; dilauroyl EDTA, triethylene tetramine dihydrochioride (TRIEN), diethylen-etriamin-pentaacetic acid (DPTA), triethylenetetramine hexaacetic acid (TTG), deferoxamine (DFO), deferasirox (DSX), dimercaprol, zinc citrate, penicilamine, succimer, editronate, sodium hexmetaphosphate, edetate calcium disodium, D-penicillamine, polyphenols, gallol, catechol, dimercaprol, tetrathiomolybdate, lactoferrin, and clioquinol and combinations thereof.

Preferably, the chelating agent is a pharmaceutically acceptable chelating agent.

In one embodiment, the chelating agent is ethylene diamine tetraacetic acid (EDTA). In another embodiment, the chelating agent is deferoxamine (DFO). In another embodiment, the chelating agent is deferasirox (DSX).

Preferably, the chelating agent has approximately the same iron affinity as EDTA, and/or approximately the same zinc affinity as EDTA. The formation constant or stability constant (log KO for EDTA at 25° C. and 0.1 M is 14.3 for $Fe^{2+}$, 25.1 for $Fe^{3+}$ and 16.5 for zinc.

In one embodiment, the chelating agent is a calcium salt of the chelating agent. Preferably, the chelating agent is CaEDTA.

In one embodiment, the chelating agent is provided in an inhaled dose form containing between 37.5 mg/dose and 300 mg/dose, between about 75 mg/dose and 200 mg/dose, between about 75 mg/dose and 100 mg/dose, between about 50 mg/dose and 200 mg/dose; preferably about 37.5 mg/dose, 50 mg/dose, 75 mg/dose, 100 mg/dose, 200 mg/dose or 300 mg/dose. The chelating agent is preferably provided in an inhaled dose form containing at least 37.5 mg/dose.

The total amount of chelating agent inhaled per day is preferably between about 37.5 mg/day and 1,200 mg/day, between about 50 mg/day and 1,200 mg/day, between about 100 mg/day and 1,000 mg/day, between about 300 mg/day and 900 mg/day, between about 400 mg/day and 800 mg/day; preferably about 300 mg/day, 500 mg/day or 600 mg/day, or at least 600 mg/day. The chelating agent may be administered up to a total dose of about 1,200 mg/day, preferably at least 37.5 mg/day.

The inhaled chelating agent is preferably delivered over a period of no more than 8 h, 7 h, 6 h, 5 h, 4 h, 3 h, 2 h, 1 h, 45 min, 30 min, 20 min, 15 min, 10 min, or 5 min. If the administration is by dry powder delivery, then the inhaled chelating agent may be delivered over a period of seconds, for example 1 second per "puff" of aerosol device or dry powder inhaler, wherein one or more puffs are administered at each time point.

Preferably the inhaled chelating agent and inhaled antibiotic is administered for at least 28 consecutive days. The inhaled chelating agent and inhaled antibiotic may be delivered for 2 days or more, 3 days, 4 days, 5 days, 6 days or 7 days. The inhaled chelating agent and inhaled antibiotic may be delivered for between 2 and 28 days, 1 week, 2 weeks, 3 weeks or 4 weeks. Some subjects may benefit from a period of "loading" the subject with antibiotic and/or the chelating agent, with a higher dose or more frequent administration over a period of days or weeks, followed by a reduced or maintenance dose.

The inhaled chelating agent and inhaled antibiotic may be provided in the absence of acidified nitrite.

Thus the present invention:
delivers a total amount of inhaled chelating agent of between 37.5 mg/day and 1,200 mg/day;
delivers a total amount of an inhaled antibiotic of between 10 mg/day and 500 mg/day;
is administered at least once per day up to six times per day, preferably up to four times a day;
is administered as a single dosage form containing both active agents, or to separate dosage forms; and/or
is administered over a period of no more than 8 h.
Preferably, the present invention:
delivers a total amount of inhaled chelating agent of between 37.5 mg/day and 1,200 mg/day;
delivers a total amount of an inhaled antibiotic of between 10 mg/day and 500 mg/day;
is administered as a single dosage form containing both active agents;
is administered once or twice per day;
is administered over a period of no more than 1 h per administration;
contains CaEDTA as the chelating agent; and/or
contains tobramycin as the antibiotic.

It has been determined that, if 75 mg of a chelating agent such as CaEDTA is inhaled, then about 0.4 mM to 1.34 mM chelating agent may be detected in the sputum from the lungs after 5 min.

The preferable amount of any chelating agent may be calculated by comparing the chelating capacity of the agent to that of CaEDTA, and then multiplying the dosage range given above by that number. The result should provide a level of chelation approximately equal to the preferred level of chelation provided by the preferred amount of EDTA.

Preferably, the antibiotic is tobramycin. However, there is no desire to limit this invention to tobramycin. Other antibiotics or anti-infectives can be used such as those selected from the group consisting of: an aminoglycoside, a tetracycline, a sulfonamide, p-aminobenzoic acid, a diaminopyrimidine, a quinolone, a β-lactam, a β-lactam and a β-lactamase inhibitor, a glycopeptide, chloraphenicol, a macrolide, penicillins, cephalosporins, corticosteroid, prostaglandin, ciprofloxacin, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, terbinafine, or any combination thereof.

Antibiotics covered by the invention include but are not limited to quinolones (such as nalidixic acid, cinoxacin, ciprofloxacin and norfloxacin and the like), sulfonamides (e.g., sulfanilamide, sulfadiazine, sulfamethaoxazole, sulfisoxazole, sulfacetamide, and the like), aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline and the like), para-aminobenzoic acid, diaminopyrimidines (such as trimethoprim, often used in conjunction with sulfamethoxazole, pyrazinamide, and the like), penicillins (such as penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil, cefinetazole, cefprozil, loracarbef, ceforanide, and the like), third generation cephalosporins (such as cefepime, cefoperazone, cefotaxime, ceftizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), beta-lactamase inhibitors (such as clavulanic acid), chloramphenicol, macrolides (such as erythromycin, azithromycin, clarithromycin, and the like), lincomycin, clindamycin, spectinomycin, polymyxin B, polymixins (such as polymyxin A, B, C, D, $E_1$(colistin A), or $E_2$, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated. Anti-infectives can include antifungal agents, including polyene antifungals (such as amphotericin B, nystatin, natamycin, and the like), flucytosine, imidazoles (such as miconazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftifine, terbinafine, or any other antibiotic and pharmaceutically acceptable salts thereof and combinations thereof. Discussion and the Examples are directed primarily toward tobramycin but the scope of the application is not intended to be limited to this antibiotic. Combinations of drugs can be used.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino) ethane salt, monomethyl-monoethanolamine salt, procaine salt and caffeine salt), a basic amino acid salt (such as arginine salt and lysine salt), tetraalkyl ammonium salt and the like, or other salt forms that enable the pulmonary hypertension reducing agent to remain soluble in a liquid medium, or to be prepared and/or effectively administered in a liquid medium, preferable an aqueous medium. The above salts may be prepared by a conventional process, for example from the corresponding acid and base or by salt interchange.

For example, one alternative embodiment, the antibiotic may be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, propionate, succinate, lactate, glycolate, malate, tartrate, citrate, maleate, fumarate, methansulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Examples of the ethers may include, but are not limited to, alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy (lower) alkyl ethers such as hydroxyethyl ether and hydroxyisopropyl ether; lower alkoxy (lower) alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl (lower) alkyl ethers such as benzyl ether, trityl ether and benzhydryl ether, or other ether forms that enable the antibiotic to remain soluble in a liquid medium, or to be prepared and/or effectively administered in a liquid medium, preferably an aqueous medium.

Examples of the esters may include, but are not limited to, aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy (lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tosyl ester, t-butylphenyl ester, salicyl ester, 3,4-di-methoxyphenyl ester and benzamidophenyl ester; and aryl(lower) alkyl ester such as benzyl ester, trityl ester and benzhydryl ester, or other ester forms that enable the antibiotic to remain soluble in a liquid medium, or to be prepared and/or effectively administered in a liquid medium, preferably an aqueous medium.

Also, the antibiotic for use in the formulations and methods provided herein may contain one or more chiral centres. Such chiral centres may be of either the (R) or (S) configuration, or may be a mixture thereof. Thus, the antibiotics for use in the formulations provided herein may be enantiomerically pure, or be stereoisomeric or diastereomeric mixtures. It is to be understood that the chiral centres of the compounds provided herein may undergo epimerization in vivo. Thus, one of skill in the art will recognize that administration of a compound in its (R) form is equivalent, for compounds that undergo epimerization in vivo, to administration of the compound in its (S) form.

In one embodiment, the antibiotic is provided in an inhaled dose form containing between 10 mg/dose and 500 mg/dose, between about 50 mg/dose and 400 mg/dose, between about 100 mg/dose and 400 mg/dose, between about 200 mg/dose and 300 mg/dose; preferably about 10 mg/dose, 20 mg/dose, 30 mg/dose, 50 mg/dose, 200 mg/dose, 250 mg/dose, 200 mg/dose or 300 mg/dose.

The total amount of antibiotic inhaled per day is preferably between about 10 mg/day and 2,000 mg/day, 10 mg/day and 1,000 mg/day, 50 mg/day and 2,000 mg/day, 250 mg/day and 2,000 mg/day, between about 300 mg/day and 1,100 mg/day, between about 500 mg/day and 1,000 mg/day, between about 800 mg/day and 1,000 mg/day; preferably about 200 mg/day, 300 mg/day, 500 mg/day, 1,000 mg/day or 1,250 mg/day.

The antibiotic is preferably delivered over a period of no more than 8 h, 7 h, 6 h, 5 h, 4 h, 3 h, 2 h, 1 h, 45 min, 30 min, 20 min, 15 min, 10 min, or 5 min per delivery. If the administration is by dry powder delivery, then the inhaled antibiotic is preferably delivered over a period of seconds, for example 1 second per puff of aerosol device or dry powder inhaler, wherein one or more puffs are administered at each time point.

If the antibiotic is tobramycin, the commonly prescribed dose of inhaled tobramycin is: TOBI® Podhaler® (dry powder)—four puffs of 28 mg (112 mg dose), twice daily for a total of 224 mg/day OR Nebulised TOBI®—300 mg in 5 ml twice daily.

If the chelating agent is delivered in a puffer, preferably each puff delivers between 37.5 mg/puff and 300 mg/puff, between about 75 mg/puff and 200 mg/puff, between about 75 mg/puff and 100 mg/puff, between about 50 mg/puff and 200 mg/puff; preferably about 37.5 mg/puff, 50 mg/puff, 75 mg/puff, 100 mg/puff, 200 mg/puff or 300 mg/puff.

Alternatively, if the chelating agent is delivered in a puffer, preferably every two puffs delivers between 37.5 mg/2×puffs and 300 mg/2×puffs, between about 75 mg/2× puffs and 200 mg/2×puffs, between about 75 mg/2×puffs and 100 mg/2×puffs, between about 50 mg/2×puffs and 200 mg/2×puffs; preferably about 37.5 mg/2×puffs, 50 mg/2× puffs, 75 mg/2×puffs, 100 mg/2×puffs, 200 mg/2×puffs or 300 mg/2×puffs.

If the antibiotic is delivered in a puffer, preferably each puff delivers between 10 mg/puff and 500 mg/puff, between about 50 mg/puff and 400 mg/puff, between about 100 mg/puff and 400 mg/puff, between about 200 mg/puff and 300 mg/puff; preferably about 10 mg/puff, 20 mg/puff, 30 mg/puff, 50 mg/puff, 200 mg/puff, 250 mg/puff, 200 mg/puff or 300 mg/puff.

Alternatively, if the antibiotic is delivered in a puffer, preferably every two puffs delivers between 10 mg/2×puffs and 500 mg/2×puffs, between about 50 mg/2×puffs and 400 mg/2×puffs, between about 100 mg/2×puffs and 400 mg/2× puffs, between about 200 mg/2×puffs and 300 mg/2×puffs; preferably about 10 mg/2×puffs, 20 mg/2×puffs, 30 mg/2× puffs, 50 mg/2×puffs, 200 mg/2×puffs, 250 mg/2×puffs, 200 mg/2×puffs or 300 mg/2×puffs.

If the composition contains both the chelating agent and the antibiotic, preferably the ratio of chelating agent:antibiotic is about 3:1, 1:10, 30:1, 3:5 or 1:1.5.

Preferably; the infection is caused by; causes or is associated with the following lung conditions: cystic fibrosis (CF); asthma; chronic obstructive pulmonary disease (COPD); pulmonary hypertension; lung cancer; pulmonary fibrosis; bronchiectasis; acute respiratory distress syndrome; tuberculosis; nontuberculous mycobacterial (NTM) pulmonary infections; pneumonia including but not limited to ventilator associated pneumonia, community acquired pneumonia, bronchial pneumonia, lobar pneumonia; infections by bacteria such as *Pseudomonas* spp, *Streptococcus pneumoniae*, *Chlamydia*, *Mycoplasma pneumonia*, *Staphylococci* spp, *Klebsiella* spp, *E. coli*, *Stenotrophomonas* spp, and fungi, including *Aspergillus*, *Scedosporium* and *Candida* sp; prophylactic treatment or prevention for conditions in which infection might arise e.g. intubated or ventilated patients; infections in lung transplant patients; bronchitis; pertussis (whooping cough); inner ear infections; streptococcal throat infections; inhalation anthrax; tularemia; or sinusitis.

Preferably, the chelating agent and/or antibiotic are administered to the subject in need between about once per day to about six times per day, more preferably about 2, 3 or 4 times per day.

Alternatively, the chelating agent and/or antibiotic may be administered to the subject in need via continuous inhalation, via a nebuliser. The nebulised chelating agent and/or antibiotic may be delivered for 8 hours, 6 hours, 4 hours, 2 hours or 1 hour, and each of these deliveries may be repeated several times within a 24 hour period.

In one embodiment, the inhaled chelating agent and the antibiotic are administered 1, 2, or 3 times a day sequentially (i.e. one after the other), or co-administered together. When the agents are co-administered, the two compounds can be mixed just prior to the administration or they can be admixed as one homogenous mixture in a self-contained preparation, provided the physical and chemical stability is maintained. In one embodiment, the inhaled chelating agent and the antibiotic are admixed as one pharmaceutical formulation and administered to subjects by inhalation. One single pharmaceutical formulation and one single treatment provide ease of use and result in better compliance of subjects.

The dose of inhaled chelating agent and antibiotic will typically be administered either nebulised or by at least one, preferably several "puffs" from an aerosol device or dry powder inhaler. For example, a subject may receive a single dose, or several doses over a day.

The total dose per day is preferably administered at least once per day or twice per day, but may be divided into three or more doses per day. Some subjects may benefit from a period of "loading" the subject with antibiotic and/or the chelating agent, with a higher dose or more frequent administration over a period of days or weeks, followed by a reduced or maintenance dose. As cystic fibrosis, COPD etc., are typically chronic conditions, subjects are expected to receive such therapy over a prolonged period of time.

Regardless of the form of the drug formulation, it is preferable to create droplets or particles for inhalation in the range of about 0.1 μm to 12 μm, or about 0.25 μm to 6 μm, preferably 1 μm to 6 μm, and more preferably about 2 μm to 4 μm. Alternatively, the particles may be 0.1 μm to 1.0 μm, 0.2 μm to 0.9 μm, 0.3 μm to 0.8 μm, 0.4 μm to 0.7 μm, or 0.5 μm. By creating inhaled particles which have a relatively narrow range of size, it is possible to further increase the efficiency of the drug delivery system and improve the repeatability of the dosing. Thus, it is preferable that the particles not only have a size in the range of 0.1 μm to 12 μm or 2 μm to 6 μm or about 3 to 4 μm but that the mean particle size be within a narrow range so that 80% or more of the particles being delivered to a subject have a particle diameter which is within +20% of the average particle size, preferably ±10% and more preferably ±5% of the average particle size.

"Particle size" is a notion introduced for comparing dimensions of solid particles, liquid particles (droplets). For droplets and aerosols, terms such as "aerodynamic diameter" and "mass median aerodynamic diameter (MMAD) are used. The definitions are given below.

"Aerodynamic diameter" is the diameter of a unit-density sphere having the same terminal settling velocity as the particle in question. It is used to predict where in the respiratory tract such particles will deposit.

"Mass Median Aerodynamic Diameter" is the geometric mean aerodynamic diameter. Fifty percent of the particles by weight will be smaller than the MMAD, 50% will be larger.

During particle sizing experiment, the suspensions contain innumerable number of particles of varying sizes in motion. When the particle-sizing machine analyses these particles, it forms a particle distribution curve, which covers the entire particle size range starting from the smallest particle, which could be 1 nm to the largest, which could be 100 μm. In the particle size distribution curve, a cumulative frequency is calculated for the particles. $D_{10}$ refers to that particular particle diameter where 10% of the particles in the suspension have a smaller diameter or equal diameter as that of the particular particle diameter.

$D_{50}$: Similar to the $D_{10}$, $D_{50}$ is the cut off diameter for 50% of the particle population in the formulation and refers to that particular particle diameter where 50% of the particles in the suspension have a smaller diameter or equal diameter as that of the particular particle diameter.

$D_{90}$: $D_{90}$ is the cut off diameter for 90% of the particle population in the formulation and refers to that particular particle diameter where 90% of the particles in the suspension have a smaller diameter or equal diameter as that of the particular particle diameter.

The term "respiratory tract" shall be taken to mean a system of cells and organs functioning in respiration, in particular the organs, tissues and cells of the respiratory tract include, lungs, nose, nasal passage, paranasal sinuses, nasopharynx, larynx, trachea, bronchi, bronchioles, respiratory bronchioles, alveolar ducts, alveolar sacs, alveoli, pneumocytes (type 1 and type 2), ciliated mucosal epithelium, mucosal epithelium, squamous epithelial cells, mast cells, goblet cells, and intraepithelial dendritic cells.

In one form of the invention, the method of treating or preventing a bacterial infection in the lung of a subject by administering a therapeutically effective or preventative effective amount of an inhaled antibiotic and a therapeutically effective or preventative effective amount of at least 37.5 mg/day of an inhaled chelating agent, each in one or more doses, wherein the or each dose of the chelating agent and/or antibiotic is administered over a period of no more than 8 h.

In one form of the invention, the method of treating a bacterial infection in the lung of a subject by administering a therapeutically effective amount of an inhaled antibiotic and a therapeutically effective amount of at least 37.5 mg/day of an inhaled chelating agent, each in one or more doses, wherein the or each dose of the chelating agent and/or antibiotic is administered over a period of no more than 8 h.

In one form of the invention, the method of preventing a bacterial infection in the lung of a subject by administering a preventative effective amount of an inhaled antibiotic and a preventative effective amount of at least 37.5 mg/day of an inhaled chelating agent, each in one or more doses, wherein the or each dose of the chelating agent and/or antibiotic is administered over a period of no more than 8 h.

In one form of the invention, the method of treating or preventing a bacterial infection in the lung of a subject comprises treating or preventing a bacterial infection in the lung of a subject in need of such treatment.

The term a "therapeutically effective amount" as used herein means an amount of the formulation, which when administered according to a desired dosage regimen, is sufficient to at least partially attain the desired therapeutic effect, or delay the onset of, or inhibit the progression of, halt, partially or fully the onset or progression of the infection and/or associated inflammation. It may further encompass delaying the onset of, or inhibiting the progression of, halting, partially or fully the onset or progression of an infection or the reversal or partially reversal of the antimicrobial sensitivity of a pathogenic microbe(s).

The term a "preventative effective amount" as used herein means an amount of the formulation, which when administered according to a desired dosage regimen, is sufficient to at least partially prevent or delay the onset of the microbial infection and/or associated inflammation.

As used herein, "treating" or "treatment" refers to inhibiting the disease or condition, i.e., arresting or reducing its development or at least one clinical or subclinical symptom thereof. "Treating" or "treatment" further refers to relieving the disease or condition, i.e., causing regression of the disease or condition or at least one of its clinical or subclinical symptoms. The benefit to a subject to be treated is either statistically significant or at least perceptible to the subject and/or the physician. In the context of treating a bacterial infection, the term treatment includes reducing or eliminating colonization by bacteria and/or multiplication of bacteria, including reducing biofilm formation or disrupting existing biofilms.

Based on the above, it will be understood by those skilled in the art that a plurality of different treatments and means of administration can be used to treat a single subject. Thus, subjects already receiving such medications, for example, as intravenous ciprofloxacin or antibiotics, etc., may benefit from inhalation of the formulations of the present invention. Some subjects may receive at least 37.5 mg/day of an inhaled chelating agent in combination with an antibiotic by inhalation. Such subjects may have symptoms of cystic fibrosis, be diagnosed as having lung infections, or have symptoms of a medical condition, which symptoms may benefit from administration to the subject of at least 37.5 mg/day of an inhaled chelating agent in combination with an antibiotic. The invention may also be used diagnostically. In an embodiment, for example, a subject may receive chelating agent and/or antibiotic as part of a procedure to diagnose lung infections, wherein one of more of the subject's symptoms improves in response to the chelating agent and/or antibiotic.

Dosage Form

The inhalable formulation may be in aerosol or dry powder form for inhalation, or in nebulised form for inhalation. Preferably, the formulation is adapted for inhalation to treat or prevent infection in the lung.

Each of the chelating agent and the antibiotic may be delivered in one single dosage form, or two or more separate dosage forms. Each of the chelating agent and the antibiotic may be delivered, for example, in several puffs of a dry powder inhaler.

The chelating agent and the antibiotic may be delivered in one single dosage form, or two separate dosage forms. If the dosage forms are separate, the dosages may be taken together (simultaneously), or one after the other. There may be a temporal separation between delivery of the dosage forms of the two actives of seconds, minutes, hours or days.

The compositions of the present invention may be delivered by puffer (pressurised metered dose inhaler, dry powder inhaler) or by nebuliser. The compositions may be provided in one device (i.e. both the chelating agent and the antibiotic in one device), or the two actives may be delivered from two different devices. For example, the two actives may be delivered by two separate puffers, two separate nebulisers, or a puffer and a nebuliser, with one active in ach device.

The inhaled chelating agent and inhaled antibiotic may be provided in the absence of acidified nitrite.

In one embodiment, the chelating agent is a calcium salt of the chelating agent. Preferably, the chelating agent is CaEDTA.

Preferably, the chelating agent is provided in an inhaled dose form containing between 37.5 mg/dose and 300 mg/dose, between about 75 mg/dose and 200 mg/dose, between about 75 mg/dose and 100 mg/dose, between about 50 mg/dose and 200 mg/dose; preferably about 37.5 mg/dose, 50 mg/dose, 75 mg/dose, 100 mg/dose, 200 mg/dose or 300 mg/dose. The chelating agent is preferably provided in an inhaled dose form containing at least 37.5 mg/dose.

The total amount of chelating agent inhaled per day is preferably between about 37.5 mg/day and 1,200 mg/day, between about 50 mg/day and 1,200 mg/day, between about 100 mg/day and 1,000 mg/day, between about 300 mg/day and 900 mg/day, between about 400 mg/day and 800 mg/day; preferably about 300 mg/day, 500 mg/day or 600 mg/day, or at least 600 mg/day. The chelating agent may be administered up to a total dose of about 1,200 mg/day, preferably at least 37.5 mg/day.

The inhaled chelating agent is preferably delivered over a period of no more than 8 h, 7 h, 6 h, 5 h, 4 h, 3 h, 2 h, 1 h, 45 min, 30 min, 20 min, 15 min, 10 min, or 5 min per delivery. If the administration is by dry powder administration, then the inhaled chelating agent is preferably delivered over a period of seconds, for example 1 second per "puff" of aerosol device or dry powder inhaler, wherein one or more puffs are administered at each time point.

For example, a 50 mg dose of CaEDTA may be administered as 4 mL nebulised solution at 33 mM (molecular mass $C_{10}H_{12}CaN_2Na_2O_8$ is 274.27 g/mol). Similarly, a 75 mg dose may be administered in 4 ml at 50 mM, or a 100 mg dose may be administered in 4 ml at 66 mM.

Preferably the antibiotic is tobramycin.

In one embodiment, the antibiotic is provided in an inhaled dose form containing between 10 mg/dose and 500 mg/dose, between about 50 mg/dose and 400 mg/dose, between about 100 mg/dose and 400 mg/dose, between about 200 mg/dose and 300 mg/dose; preferably about 10 mg/dose, 20 mg/dose, 30 mg/dose, 50 mg/dose, 200 mg/dose, 250 mg/dose, 200 mg/dose or 300 mg/dose.

The total amount of antibiotic inhaled per day is preferably between about 10 mg/day and 2,000 mg/day, 10 mg/day and 1,000 mg/day, 50 mg/day and 2,000 mg/day, 250 mg/day and 2,000 mg/day, between about 300 mg/day and 1,100 mg/day, between about 500 mg/day and 1,000 mg/day, between about 800 mg/day and 1,000 mg/day; preferably about 200 mg/day, 300 mg/day, 500 mg/day, 1,000 mg/day or 1,250 mg/day.

The dose of inhaled antibiotic is preferably administered over a period of no more than 8 h, 7 h, 6 h, 5 h, 4 h, 3 h, 2 h, 1 h, 45 min, 30 min, 20 min, 15 min, 10 min, or 5 min per administration. If the administration is by dry powder delivery, then the inhaled antibiotic is preferably administered over a period of seconds, for example 1 second per "puff" of aerosol device or dry powder inhaler, wherein one or more puffs are administered at each time point.

Preferably, the chelating agent and/or antibiotic is administered to the subject in need between about once per day to about six times per day, more preferably about two times per day.

Alternatively, the chelating agent and/or antibiotic may be administered to the subject in need via continuous inhalation, via a nebuliser. The nebulised formulation may be delivered for 8 hours, 6 hours, 4 hours, 2 hours or 1 hour, and each of these deliveries may be repeated several times within a 24-hour period.

The formulations of the invention may be administered to a subject using a disposable package and portable, handheld, battery-powered device, such as the AERx device (U.S. Pat. No. 5,823,178, Aradigm, Hayward, Calif.). Alternatively, the formulations of the instant invention may be carried out using a mechanical (non-electronic) device. Other inhalation devices may be used to deliver the formulations including conventional jet nebulizers, ultrasonic nebulizers, soft mist inhalers, dry powder inhalers (DPIs), metered dose inhalers (MDIs), condensation aerosol generators, and other systems.

For use as aerosols, the compounds of the present invention in solution or suspension may be packaged in a pressurized aerosol container together with suitable propellants, for example, hydrocarbon propellants like propane, butane, or isobutane with conventional adjuvants. A dry powder inhaler is a system operable with a source of pressurized air to produce dry powder particles of a pharmaceutical formulation that is compacted into a very small volume. For inhalation, the system has a plurality of chambers or blisters each containing a single dose of the pharmaceutical formulation and a select element for releasing a single dose.

An aerosol may be created by forcing drug through pores of a membrane which pores have a size in the range of about 0.25 to 6 μm (U.S. Pat. No. 5,823,178). When the pores have this size the particles which escape through the pores to create the aerosol will have a diameter in the range of 0.5 to 12 μm. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that an object of some embodiments is to provide aerosolized particles having a diameter in the range of about 0.5 to 12 μm.

Excipients

The above-exemplified forms of the formulations described herein can be manufactured by methods well known to one of skill in the art of formulation science. Additionally, the formulations described herein may include other optional excipients to aid in the manufacturing and/or administration of the formulations described herein. Non-limiting examples of such excipients are well known in the art and include flavourings, colorants, palatants, antioxidants, viscosity modifying, tonicity agents, drug carriers, sustained-release agents, comfort-enhancing agents, emulsifiers, solubilizing aids, lubricants, binding agents and other stabilizing agents to aid in the manufacturing and/or administration of the formulations.

Preferably, the present formulation is sterile. In another embodiment, the formulation of the present invention is stable.

Further, buffering agents may be added to adjust the pH level of the formulation. Preferably, the formulations of the present invention contain tris(hydroxymethyl)aminomethane (TRIS, also as known as THAM, or tromethamine) as a buffering agent. TRIS may have a further effect in increasing the effect of bacterial killing by EDTA. Preferably, TRIS is added to the formulations of present invention both to buffer the formulation and to increase the effectiveness of the EDTA and/or antibiotic in treating or preventing bacterial infections.

Moreover, the formulations of the present invention may contain an antimicrobial preservative.

Preferably, the pH of the formulations of the present invention is between about 6.5 and 8.0, more preferably about 7.0 and 7.4. It has previously been found that bacteria become more resistant to anti-microbial therapy the more the pH drops. The preferable pH assists in avoiding bacterial resistance to formulations an inhaled chelating agent and/or an antibiotic.

The inhaled chelating agent and inhaled antibiotic may be provided in the absence of acidified nitrite.

In one alternate embodiment, the formulation of the present invention may comprise a preservative, suspending agent, wetting agent, tonicity agent and/or diluent. The formulations provided herein may comprise from about 0.01% to about 90%, or about 0.01% to about 50%, or about 0.01% to about 25%, or about 0.01% to about 10%, or about 0.01% to about 5% of one or more pharmacologically suitable suspending fluids which is physiologically acceptable upon inhalation. Pharmacologically suitable fluids for use herein include, but are not limited to, polar solvents, including, but not limited to, compounds that contain hydroxyl groups or other polar groups. Solvents include, but are not limited to, water or alcohols, such as ethanol, isopropanol, and glycols including propylene glycol, polyethylene glycol, polypropylene glycol, glycol ether, glycerol and polyoxyethylene alcohols. Polar solvents also include protic solvents, including, but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in inhaled drugs.

In one embodiment, the formulations described herein may be aqueous and contain 0-90% water. In other embodiments, the aqueous formulations described herein may contain 20-80% water. In still other embodiments, aqueous formulations may contain 50-70% water. The water may further comprise water that is plain, distilled, sterile, demineralized or deionized.

Alternatively, the formulation may be non-aqueous and contain no water, or negligible amounts of water (e.g. below 1%, below 0.1%, below 0.01%).

In one embodiment, the formulation further comprises one or more pharmaceutically or physiologically acceptable carriers, diluents or excipients.

In addition to or in lieu of sterilization, the formulations of the present invention may contain a pharmaceutically acceptable preservative to minimize the possibility of microbial contamination. Additionally, a pharmaceutically-acceptable preservative may be used in the present formulations to increase the stability of the formulations. It should be noted, however, that any preservative must be chosen for inhalation safety, as the treated tissues may be sensitive to irritants. Preservatives suitable for use herein include, but are not limited to, those that protect the solution from contamination with pathogenic particles, including phenylethyl alcohol, benzalkonium chloride or benzoic acid, or benzoates such as sodium benzoate and phenylethyl alcohol. In certain embodiments, the formulations herein comprise from about 0.001% to about 10.0% w/w of benzalkonium chloride, or from about 0.01% v/w phenylethyl alcohol. Preserving agents may also be present in an amount from about 0.001% to about 1%, preferably about 0.002% to about 0.02%, more preferably 0.02% w/w.

The formulations provided herein may also comprise from about 0.001% to about 90%, or about 0.001% to about 50%, or about 0.001% to about 25%, or about 0.001% to about 10%, or about 0.001% to about 1% of one or more emulsifying agent, wetting agent, or suspending agent. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan monooleate, polyoxyethylene (20) sorbitan monopalmitate, polyoxyethylene (20) sorbitan monostearate; lecithins; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-21 actylate; calcium stearoyl-2-lactylate; stearoyl tartrate; sorbitan monostearate; sorbitan tristearate; sorbitan monolaurate; sorbitan monooleate; sorbitan monopalmitate; extract of *quillaia*; polyglycerol esters of dimerised fatty acids of soya bean oil; oxidatively polymerised soya bean oil; and pectin extract.

The formulations of the present invention may comprise from about 0.001% to about 5% by weight of a humectant to inhibit drying of the mucous membrane and to prevent irritation. Any of a variety of pharmaceutically-acceptable humectants can be employed, including sorbitol, propylene glycol, polyethylene glycol, glycerol or mixtures thereof, for example.

The formulation of the present invention may further comprise an adjuvant, such as: a bronchodilator, another anti-inflammatory agent, a surfactant, aspirin, or ethyl alcohol.

Bronchodilators optionally used in the formulations of the invention include but are not limited to $\beta_2$-adrenergic receptor agonists (such as albuterol, bambuterol, salbutamol, salmeterol, formoterol, arformoterol, levosalbutamol, procaterol, indacaterol, carmoterol, milveterol, procaterol, terbutaline, and the like), and antimuscarinics (such as trospium, ipratropium, glycopyrronium, aclidinium, and the like). Combinations of drugs may be used.

Additional anti-inflammatories that may optionally be used in the formulations of the invention include but are not limited to inhaled corticosteroids (such as beclometasone, budesonide, ciclesonide, fluticasone, etiprednol, mometasone, and the like), leukotriene receptor antagonists and leukotriene synthesis inhibitors (such as montelukast, zileuton, ibudilast, zafirlukast, pranlukast, amelubant, tipelukast, and the like), cyclooxygenase inhibitors (such as ibuprofen, ketoprofen, ketorolac, indometacin, naproxen, zaltoprofen, lornoxicam, meloxicam, celecoxib, lumiracoxib, etoricoxib, piroxicam, ampiroxicam, cinnoxicam, diclofenac, felbinac, lornoxicam, mesalazine, triflusal, tinoridine, iguratimod, pamicogrel, and the like). Combinations of drugs may be used. Aspirin may also be added to act as an anti-inflammatory agent.

Antioxidants such as glutathione and vitamin E, zinc and zinc salts of EDTA, may be added.

Surfactants covered by the invention include but are not limited to synthetic surfactant (Exosurf®), dipalmitoylphosphatidylcholine and oleic acid. Combinations of drugs may be used.

Ethyl alcohol vapour acts as an anti-foaming agent in the lungs and makes sputum more liquid, which can aid breathing and reduce lung oedema. Ethanol may be added to the formulations of the present invention at between 0.5% and 60%, more preferably between 1 and 40%, 1 and 20%, or 1 and 10%. The ethanol may be added at 1%, 2%, 3%, 4%, 5%, 6%, 7%, 8%, 9%, 10%, 15%, 20%, 25%, 30%, 35%, 40%, 45%, 50% 55% or 60%.

The invention also relates to the use of an inhaled chelating agent used in combination with an inhaled antibiotic, wherein at least 37.5 mg/day of the inhaled chelating agent is delivered, wherein the or each dose of the chelating agent and/or antibiotic is administered over a period of no more than 8 h in further combination with other drugs given via inhalation. These other drugs may include a nucleotide sequence which may be incorporated into a suitable delivery vector such as a plasmid or viral vector. The other drug may be a therapeutic nucleotide sequence (DNA, RNA, siRNA), enzymes to reduce the viscoelasticity of the mucus such as DNase and other mucolytic agents, chemicals to upregulate the chloride ion channel or increase flow of ions across the cells, nicotine, P2Y2 agonists, elastase inhibitors including α-1 antitrypsin (AAT), N-acetylcysteine, antibiotics and cationic peptides, such as lantibiotics, and specifically duramycin, short-acting bronchodilators (e.g., β2-adrenergic receptor agonists like albuterol or indacaterol), M3 muscarinic antagonists (e.g., ipatropium bromide), K$^+$-channel openers, long-acting bronchodilators (e.g., formoterol, salmeterol), steroids (e.g., budesonide, fluticasone, triamcinolone, beclomethasone, ciclesonide, etc.), xanthines, leukotriene antagonists (e.g., montelukast sodium), phosphodiesterase 4 inhibitors, adenosine receptor antagonists, other miscellaneous anti-inflammatories (e.g., Syk kinase inhibitors (AVE-0950), tryptase inhibitors (AVE-8923 & AVE-5638), tachykinin antagonists (AVE-5883), inducible nitric oxide synthase inhibitors (GW-274150) and others), transcription factor decoys, TLR-9 agonists, antisense oligonucleotides, siRNA, DNA, CGRP, lidocaine, inverse β2-agonists, anti-infective oxidative therapies, cytokine modulators (e.g., CCR3 receptor antagonists (GSK-766994, DPC-168, AZD-3778), TNF-α production inhibitors (LMP-160 & YS-TH2), and IL-4 antagonists (AVE-0309)), small molecule inhibitors of IgE, cell adhesion molecule (CAM) inhibitors, small molecules targeting the VLA4 receptor or integrin .alpha.4.beta.1 (e.g., R-411, PS-460644, DW-908e, & CDP-323), immunomodulators including those that block T-cell signalling by inhibition of calcineurin (Tacrolimus), heparin neutralizers (Talactoferrin a), cytosolic PLA2 inhibitors (Efipladib), or combinations thereof. If the subject in need has CF, then they may also be administered standard medications such as ivacaftor, pulmozyme, mannitol, or other approved drugs according to standard practise, in combination with the formulations of the present invention.

The delivery of the combination products may be achieved by combining the drugs into one stable formulation, or providing the drugs in separate containers to be combined at the time of administration or alternatively by sequentially delivering the products.

Preferably, the formulations of the present invention are stable. As used herein, the stability of formulations provided herein refers to the length of time at a given temperature that at least 80%, 85%, 90% or 95% of the initial amount of drug substance, e.g., chelating agent and antibiotic, is present in the formulation. For example, the formulations provided herein may be stored between about 15° C. and about 30° C., and remain stable for at least 1, 2, 12, 18, 24 or 36 months. Also, the formulations may be suitable for administration to a subject in need thereof after storage for more than 1, 2, 12, 18, 24 or 36 months at 25° C. Also, in another alternative embodiment, using Arrhenius Kinetics, more than 80%, or more than 85%, or more than 90%, or more than 95% of the initial amount of drug substance (e.g., chelating agent and antibiotic) remains after storage of the formulations for more than 1, 2, 12, 18, 24 or 36 months between about 15° C. and about 30° C.

As used herein, the statement that a formulation is stable during "long term storage" means that the formulation is suitable for administration to a subject in need thereof when it has an estimated shelf-life of at least 1, 2 or 3 months usage time at 25° C. and at least or equal to 1, 2 or 3 years storage time at 5° C. In certain embodiments herein, using Arrhenius kinetics, >80% or >85% or >90% or >95% estimated chelating agent and antibiotic remains after such storage.

The term "infection" as used herein means and/or colonization by a microorganism and/or multiplication of a micro-organism, in particular, a bacterium. The bacterium can be Gram-negative such as a member of the *Pseudomonas* genus, or a Gram-positive such as *S. aureus*. The infection may be unapparent or result in local cellular injury. The infection may be localized, subclinical and temporary or alternatively may spread by extension to become an acute or chronic clinical infection. The infection may also be a past infection wherein residual antigen from a protein associated with anaerobic growth of *P. aeruginosa*, or alternatively, reactive host antibodies that bind to isolated from a protein of *P. aeruginosa* protein or peptides there from, remain in the host. The infection may also be a latent infection, in which the microorganism is present in a subject, however the subject does not exhibit symptoms of disease associated with the organism. Preferably, the infection is a respiratory tract infection, preferably a respiratory tract infection caused by *P. aeruginosa*.

Methods for Manufacturing a Medicament

The present invention provides for the use of an inhaled chelating agent for the manufacture of a medicament for the treatment of infection, wherein the inhaled chelating agent will be used in combination with an inhaled antibiotic, wherein at least 37.5 mg/day of the inhaled chelating agent is delivered, wherein the or each dose of the chelating agent and/or antibiotic is administered over a period of no more than 8 h.

The present invention provides for the use of an inhaled antibiotic for the manufacture of a medicament for the treatment of infection, wherein the inhaled antibiotic will be used in combination with an inhaled chelating agent, wherein at least 37.5 mg/day of the inhaled chelating agent is delivered, wherein the or each dose of the chelating agent and/or antibiotic is administered over a period of no more than 8 h.

The present invention provides for the use of an inhaled chelating agent and an inhaled antibiotic for the manufacture of a medicament for the treatment of infection, wherein at least 37.5 mg/day of the inhaled chelating agent is delivered, wherein the or each dose of the chelating agent and/or antibiotic is administered over a period of no more than 8 h. Preferably the medicament does not contain acidified nitrite.

Preferably the chelating agent is administered between one and four times daily, up to a total dose of between 37.5 mg/day to 1,200 mg/day. Preferably, the chelating agent is administered over a period of no more than 1 h. Preferably the chelating agent is CaEDTA.

Preferably the antibiotic is administered between one and four times daily, up to a total dose of between about 10 mg/day and 2,000 mg/day, preferably 1,000 mg/day. Preferably, the dosage form containing the antibiotic is administered over a period of no more than 1 h. Preferably the antibiotic is tobramycin.

Kits

The present invention provides a kit for treating or preventing a bacterial infection in the lung of a subject containing (i) at least 37.5 mg of an inhaled chelating agent; and (ii) instructions for use, wherein the instructions provide that at least 37.5 mg/day of the inhaled chelating agent is delivered with an inhaled antibiotic, wherein the or each dose of the chelating agent and/or antibiotic is administered over a period of no more than 8 h.

The present invention provides a kit for treating or preventing a bacterial infection in the lung of a subject containing (i) an inhalable antibiotic; and (ii) instructions for use, wherein the instructions provide that the antibiotic is delivered with at least 37.5 mg/day of an inhaled chelating agent is delivered, wherein the or each dose of the chelating agent and/or antibiotic is administered over a period of no more than 8 h.

The present invention provides a kit for treating or preventing a bacterial infection in the lung of a subject containing (i) at least 37.5 mg of an inhaled chelating agent and an inhalable antibiotic; and (ii) instructions for use, wherein the instructions provide that at least 37.5 mg/day of the inhaled chelating agent is delivered, wherein the or each dose of the chelating agent and/or antibiotic is administered over a period of no more than 8 h.

Preferably the inhaled chelating agent and/or inhaled antibiotic are provided in the absence of acidified nitrite.

Preferably the chelating agent is administered between one and four times daily, up to a total dose of between 37.5 mg/day to 1,200 mg/day. Preferably, the chelating agent is administered over a period of no more than 1 h. Preferably the chelating agent is CaEDTA.

Preferably the antibiotic is administered between one and four times daily, up to a total dose of between about 10 mg/day and 2,000 mg/day, preferably 1,000 mg/day. Preferably, the dosage form containing the antibiotic is administered over a period of no more than 1 h. Preferably the antibiotic is tobramycin.

The chelating agent and/or antibiotic may be premeasured, premixed and/or pre-packaged. Preferably, the inhalation solution is sterile.

The kit of the present invention may also include instructions designed to facilitate user compliance. Instructions, as used herein, refers to any label, insert, etc., and may be positioned on one or more surfaces of the packaging material, or the instructions may be provided on a separate sheet, or any combination thereof. For example, in an embodiment, the kit of the present invention comprises instructions for administering the formulations of the present invention. In one embodiment, the instructions indicate that the formulation of the present invention is suitable for the treatment of a lung infection. Such instructions may also include instructions on dosage, as well as instructions for administration via nebulizer or dry powder inhaler.

The inhaled chelating agent and the antibiotic can be packaged individually so to allow a practitioner or user to formulate each into a pharmaceutical formulation as needed. Alternatively, the pharmaceutical formulation comprising an inhaled chelating agent and the antibiotic can be packaged together, thereby requiring de minimus formulation by the practitioner or user. In any event, the packaging should maintain chemical, physical, and aesthetic integrity of the active ingredients.

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, displacement and field strength etc.). A range of values will be understood to include all values within the range, including the values defining the range, and values adjacent to the range which lead to the same or substantially the same outcome as the values immediately adjacent to that value which defines the boundary to the range. Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

Further features of the present invention are more fully described in the following non-limiting Examples. This description is included solely for the purposes of exemplifying the present invention. It should not be understood as a restriction on the broad description of the invention as set out above.

Microplate Testing of Antibiotics and Adjuvants

Growth method 1: Cells were grown in M9 medium supplemented with arginine and $MgSO_4$, in polystyrene 96-well plates (Nunc) by seeding each well with 2004 of an overnight culture of *P. aeruginosa* strain WACC 91 and incubating at 37° C. for 24 hours.

Growth method 2: Overnight cultures of the relevant strain of *P. aeruginosa* were grown in M63 medium supplemented with glucose (0.5% w/v), casamino acids (0.2% w/v) and MgSO$_4$ (1 mM) at 35° C. with shaking. 96-well microplates containing M63 with serial dilutions of antibiotics and adjuvants as indicated were inoculated to OD$_{600\ nm}$ 0.01 in a final volume of 200 µl. Plates were incubated at 35° C. overnight without shaking.

Anaerobic cultures were incubated in a closed chamber with anaerobic sachets to remove oxygen.

Planktonic growth was monitored by OD reading or plate counting. Biofilms were quantified by staining with 40 µl of crystal violet stain (1% w/v in water) for 10 min at room temperature, washing twice with 250 µl of water, dissolving the stain in 250 µl of 50% ethanol and reading optical density at 595 nm.

Biofilm disruption or killing was monitored by growing cells as described and removing planktonic cells by pipetting. The attached biofilm was washed carefully with sterile PBS three times, and fresh medium containing the treatment (tobramycin alone or together with CaNa$_2$EDTA in solution, tris-buffered solution, or as dry powder particles) was added. Plates were incubated for a further 24 hours and metabolic activity was measured. Biofilms were washed as described above, then fresh medium containing 0.02% w/v resazurin was added. Plates were shaken briefly to mix, then incubated at 37° C. for 2 hours. Metabolic activity, as reflected by the conversion of resazurin to resafurin, was assessed by measuring the increase in fluorescence at an excitation wavelength of 530 nm with detection at 590 nm.

Checkerboard assays of other species were carried out using growth method 1, apart from the following variations. *Burkholderia cepacia* was incubated at 30° C., and other bacteria were incubated at 37° C. *Streptococcus pyogenes* and *Streptococcus pneumoniae* were grown in Todd Hewitt Broth, and *Staphylococcus aureus* was grown in Veal Infusion Broth.

Example 1: A High Concentration of Chelating Agent Enhances the Efficacy of Tobramycin Against *P. aeruginosa* Planktonic Cells and Biofilms EDTA can make bacteria sensitive to much lower concentrations of antibiotics. Cells of *P. aeruginosa* WACC91 were grown according to method 1 and tested in a checkerboard assay against tobramycin and CaEDTA in varying concentrations.

FIG. 1 shows that for *P. aeruginosa* planktonic cells grown in aerobic conditions, CaEDTA lowers the MIC of tobramycin and that this effect is enhanced by tris buffering. FIG. 2 shows that CaEDTA lowers the concentration of tobramycin required to block *P. aeruginosa* biofilm formation. Many antibiotics work very poorly under anaerobic conditions due to slower metabolism. This is a particular challenge in the chronic lung infections of patients with cystic fibrosis, where bacteria form biofilms inside anaerobic pockets of trapped airway mucus. FIGS. 3 and 4 demonstrate that effects seen in FIGS. 1 and 2 are maintained under anaerobic conditions, especially for buffered CaEDTA.

Figure 6:
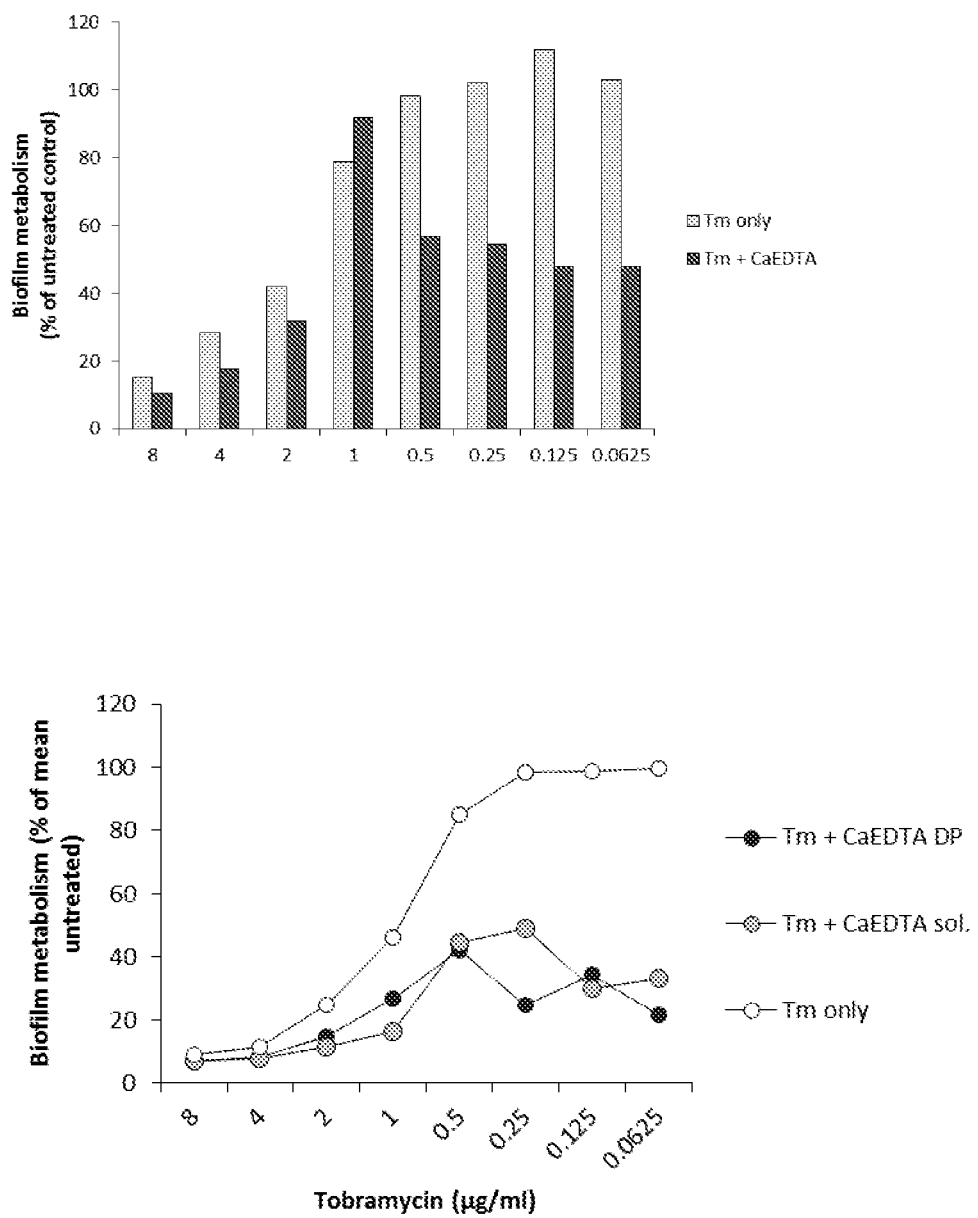
Figure 9A:
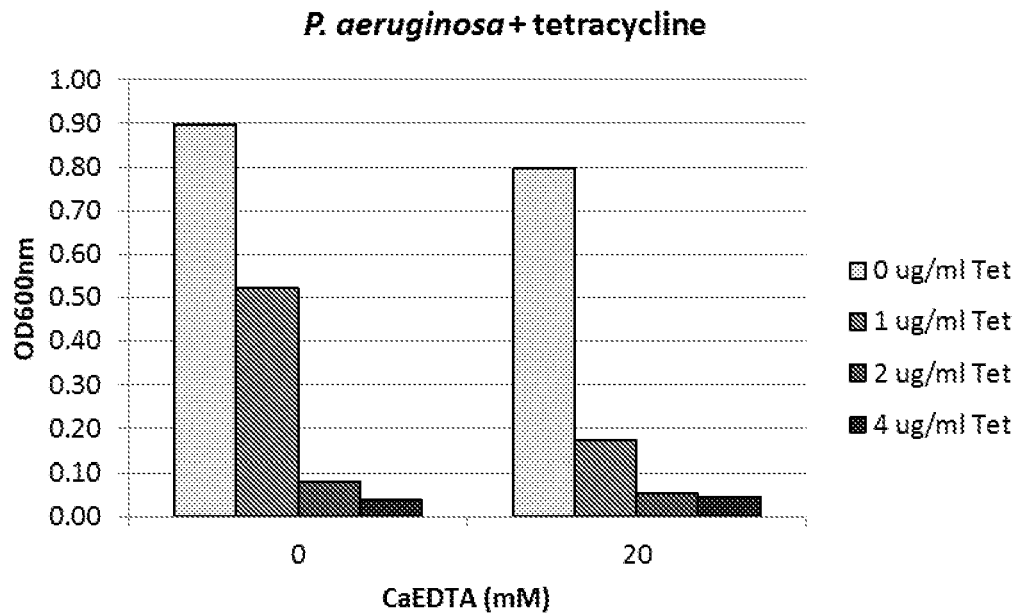
Figure 9B:
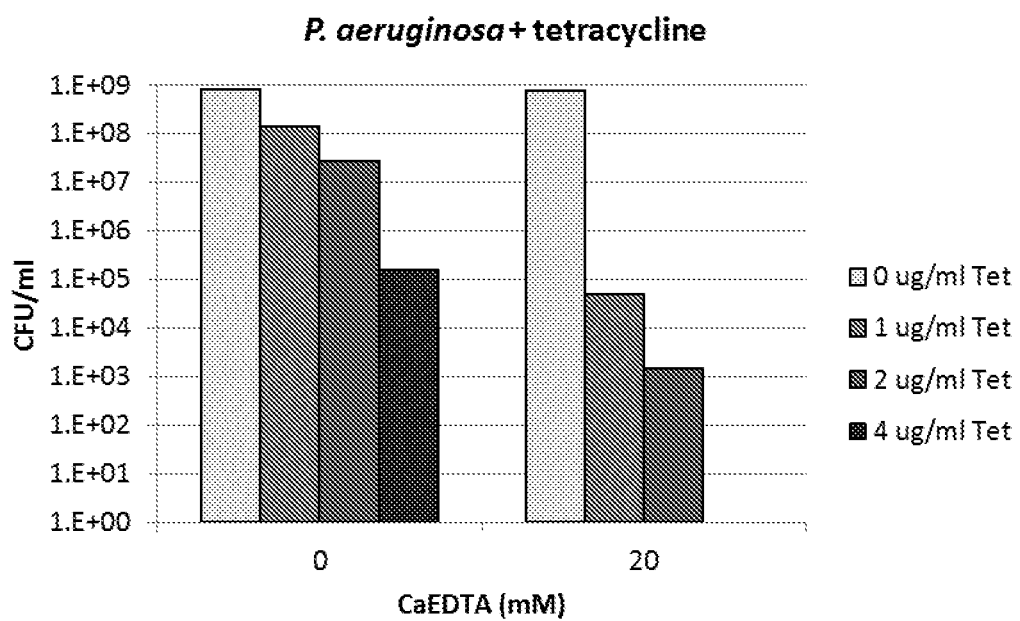
Figure 10A:
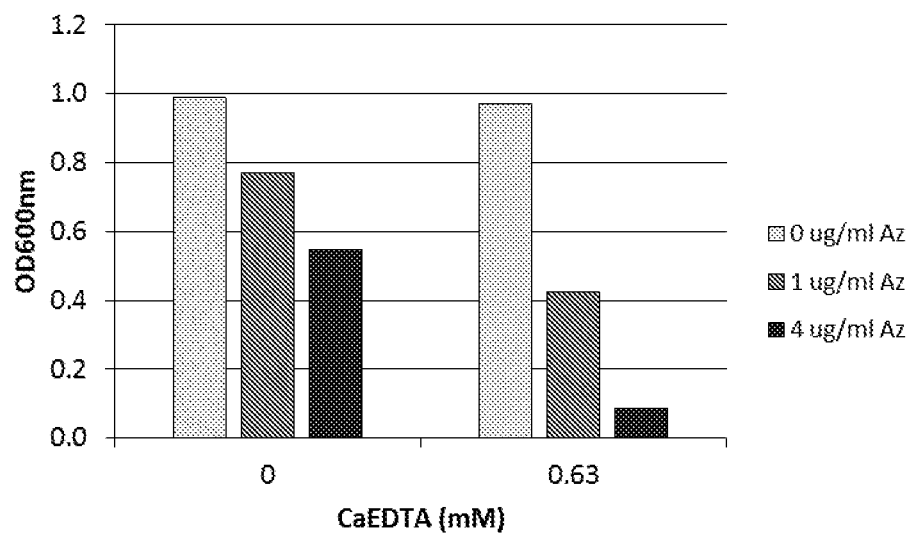
Figure 10B:
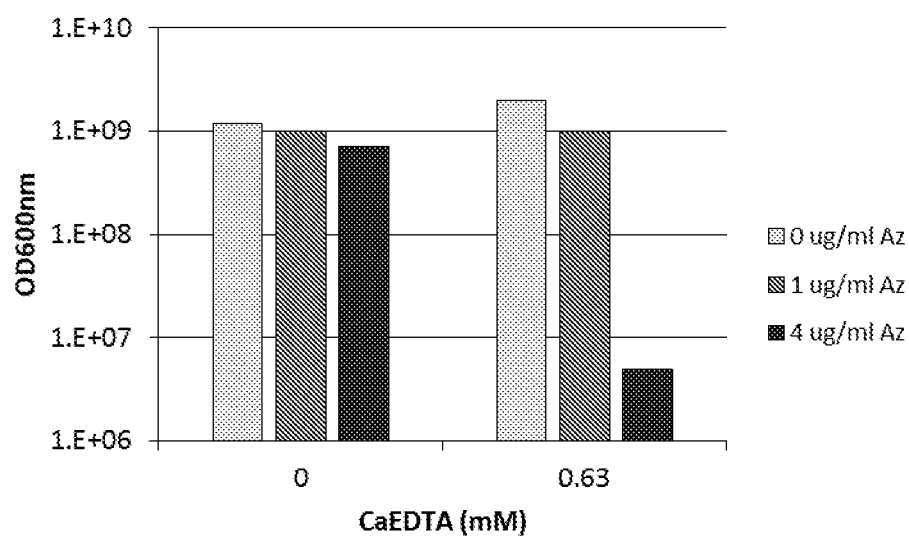
Figure 11A:
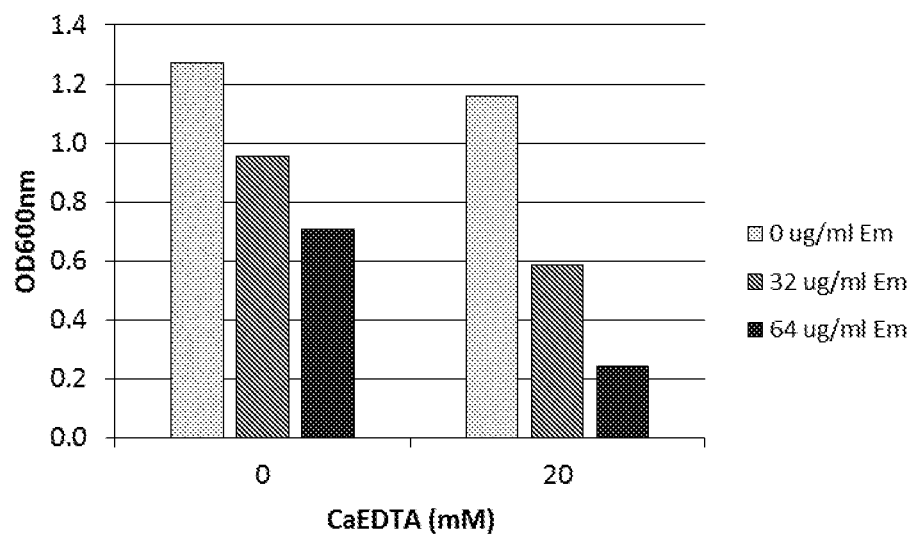
Figure 11B:
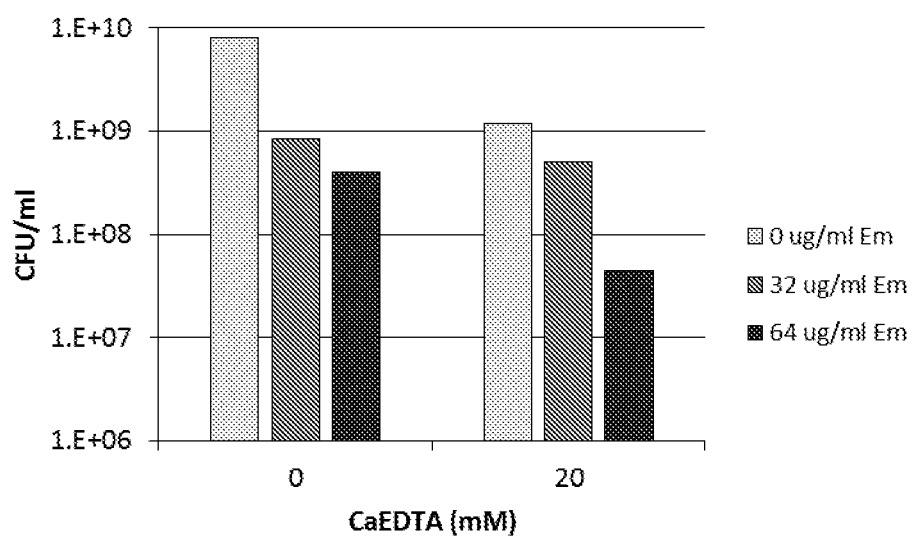

It is known from previous publications that tobramycin and other antibiotics at sub-MIC concentrations in fact increase biofilm formation in *P. aeruginosa* (Hoffman, L. R., D'Argenio, D. A., MacCoss, M. J., Zhang, Z., Jones, R. A., and Miller, S. I. (2005). Aminoglycoside antibiotics induce bacterial biofilm formation. Nature 436, 1171-1175; Jones, C., Allsopp, L., Horlick, J., Kulasekara, H., and Filloux, A. (2013). Subinhibitory concentration of kanamycin induces the *Pseudomonas aeruginosa* type VI secretion system. PLoS One 8, e81132.). FIG. 5 shows that this is indeed the case for tobramycin alone, but that the effect is reversed and planktonic and biofilm growth is reduced in both aerobic and anaerobic conditions when CaEDTA is added. In addition to preventing the formation of new biofilms, FIG. 6 further shows that CaEDTA increases the efficacy of tobramycin against existing *P. aeruginosa* biofilms as measured by metabolic activity.

Example 2: A High Concentration of Chelating Agent Enhances the Antibacterial Efficacy of a Range of Different Antibiotics Against *P. aeruginosa*

The effects seen in the previous example are not specific to the antibiotic tobramycin, which belongs to the aminoglycoside class of antibiotics. Cells were grown according to method 2 and challenged with buffered CaEDTA and a series of clinically relevant antibiotics of different classes with different modes of action. FIGS. 7-12 show that buffered CaEDTA increases the sensitivity of *P. aeruginosa* planktonic cells and biofilms as indicated of the antibiotics methicillin (beta-lactam, FIG. 7), carbenicillin (carboxypenicillin, FIG. 8), tetracycline (tetracyclines, FIG. 9), aztreonam (monobactam; commercial product Azactam, FIG. 10), erythromycin (macrolide, FIG. 11), and colistin (polymyxin, FIG. 12).

Example 3: Different Chelating Agents Enhance the Efficacy of Tobramycin Against *P. aeruginosa*

Figures 12, 13:
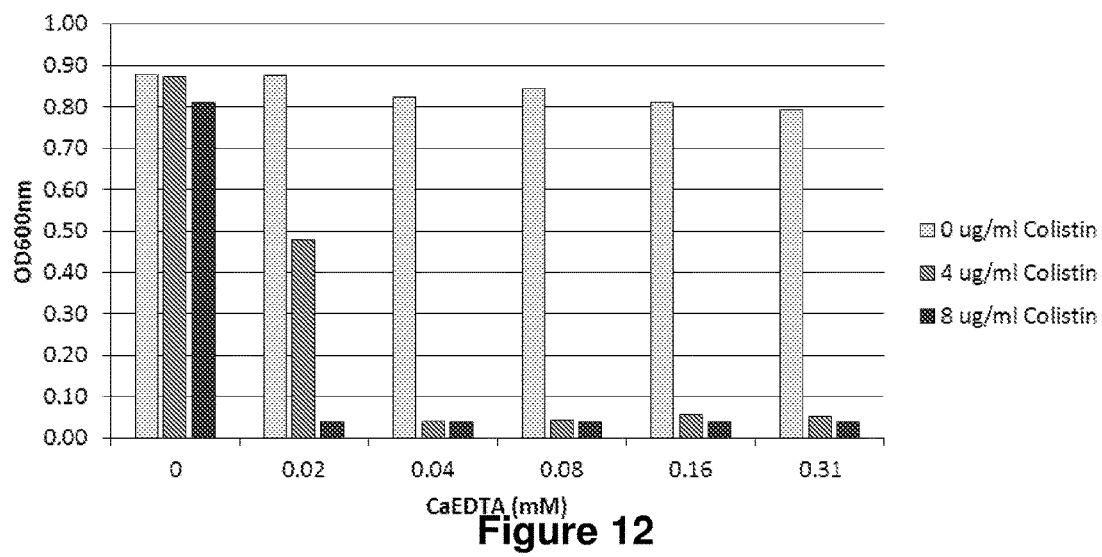

The effects of chelation on antibiotic sensitivity, as observed in the previous examples, is not limited to the chelating agent EDTA. Cells were grown according to method 2 and challenged with different concentrations of tobramycin. FIGS. 13 and 14 show that ethylene glycol tetraacetic acid (EGTA) and diethylenetriaminepentaacetic acid (DTPA) also reduce the MIC of tobramycin against *P. aeruginosa* in a concentration-dependent manner, similar to that observed for EDTA.

Example 4: A High Concentration of Chelating Agent Enhances the Efficacy of Antibiotics Against a Variety of Bacterial Species The sensitization of bacteria to antibiotics by chelating agents is not specific to *P. aeruginosa*, but has been demonstrated for a variety of other bacterial species. FIGS. 15-21 show that different species of bacteria that are known to cause lung infections in humans are sensitized to clinically relevant antibiotics in the presence of buffered CaEDTA. The effect is seen in both gram-negative and gram-positive bacteria, which often respond to very different antimicrobial agents.

Figures 15A, 15B:
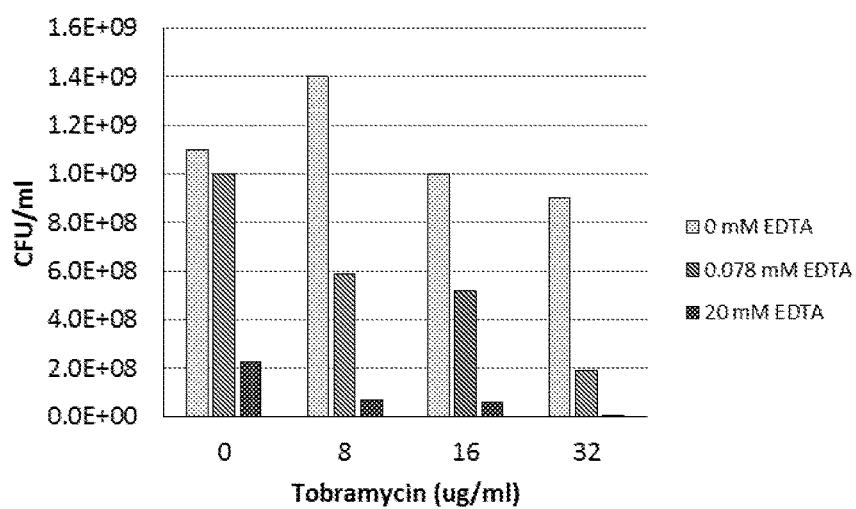
FIG. 15: *Burkholderia cepacia* planktonic cells vs tobramycin and CaEDTA.
Figure 20A:
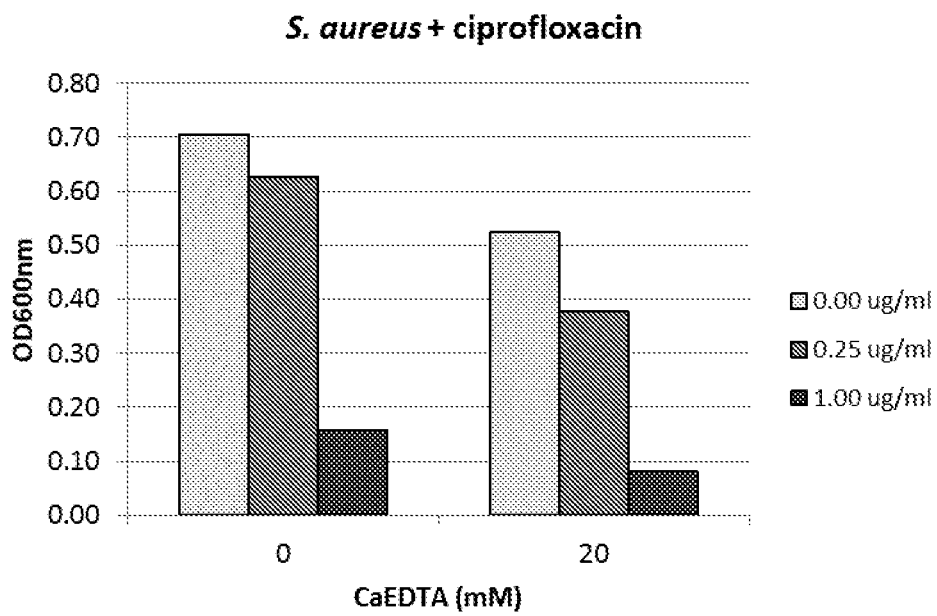
FIG. 20A: OD600 nm.
Figure 20B:
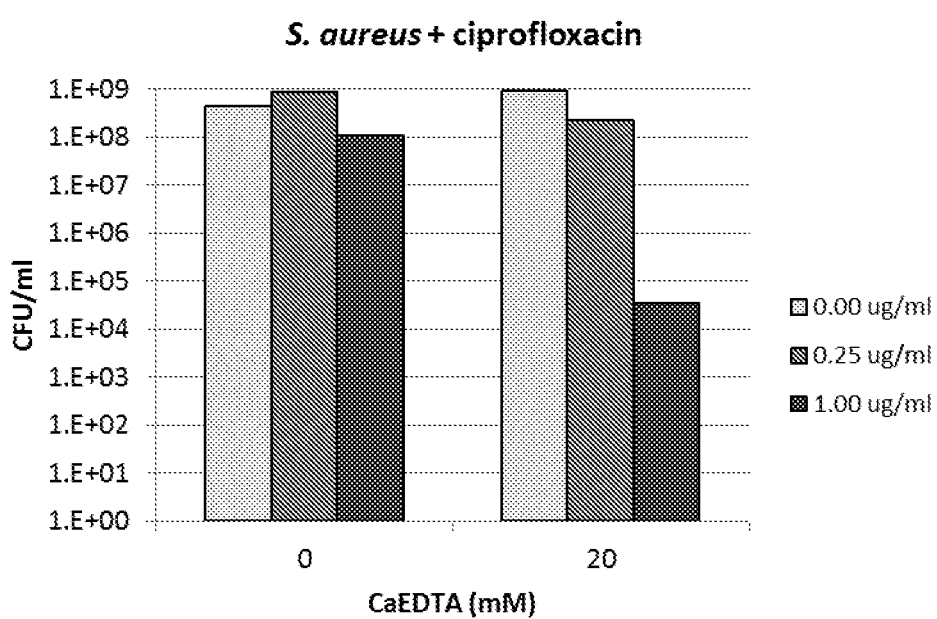
FIG. 20B: CFU/ml.

*Burkholderia cepacia* is a gram-negative bacterium that can causes serious respiratory infections in patients with cystic fibrosis (Silva Filho, L. V., Ferreira Fde, A., Reis, F. J., Britto, M. C., Levy, C. E., Clark, O., and Ribeiro, J. D. (2013). *Pseudomonas aeruginosa* infection in patients with cystic fibrosis: scientific evidence regarding clinical impact, diagnosis, and treatment. J Bras Pneumol 39, 495-512.). FIGS. 15 and 16 show that the MIC of *B. cepacia* to two different classes of antibiotics, namely tobramycin (aminoglycoside) and ciprofloxacin (fluoroquinolone), is lowered in the presence of buffered CaEDTA. FIG. 17 shows that planktonic cells (FIG. 17A) and biofilms (FIG. 17B) of *Klebsiella pneumoniae*, another gram-negative pulmonary pathogen, are sensitized to the antibiotic colistin in the presence of buffered CaEDTA.

For gram-positive bacteria, FIGS. 18-21 show reduced MIC values in the presence of buffered CaEDTA for *Streptococcus pyogenes* against tetracycline (FIG. 18), *Staphylococcus aureus* MRSA against vancomycin (FIG. 19), and MSSA (FIG. 20) and MRSA (FIG. 21) planktonic cells and biofilms against ciprofloxacin.

Example 5: A High Concentration of Chelating Agent Increases Bacterial Killing by Antibiotics The previous examples demonstrate that chelating agents can prevent growth of planktonic cells and biofilms at lower antibiotic concentrations than antibiotics alone. This is likely a result of increased antibiotic killing. Challenge microorganisms were grown on solid agar and suspended in 0.9% Sodium Chloride (SCl) to create a challenge suspension. A 0.1 mL aliquot of the challenge suspension containing approximately $1 \times 10^8$ colony forming units was then inoculated into 10 mL Cation-Adjusted Mueller Hinton Broth (CaMHB) with the appropriate antibiotic or antibiotic with chelator, as indicated, and mixed thoroughly. The challenge suspension/antibiotic mixtures were then incubated at 35 degrees C. for the exposure time. At each timepoint, 0.1 mL aliquots were removed and placed into 9.9 mL of Butterfield's Phosphate Buffer with product neutralizers, mixed thoroughly by vortexing, and plated using the appropriate agar. Recovered colonies were enumerated using a hand-tally counter.

Figure 21A:
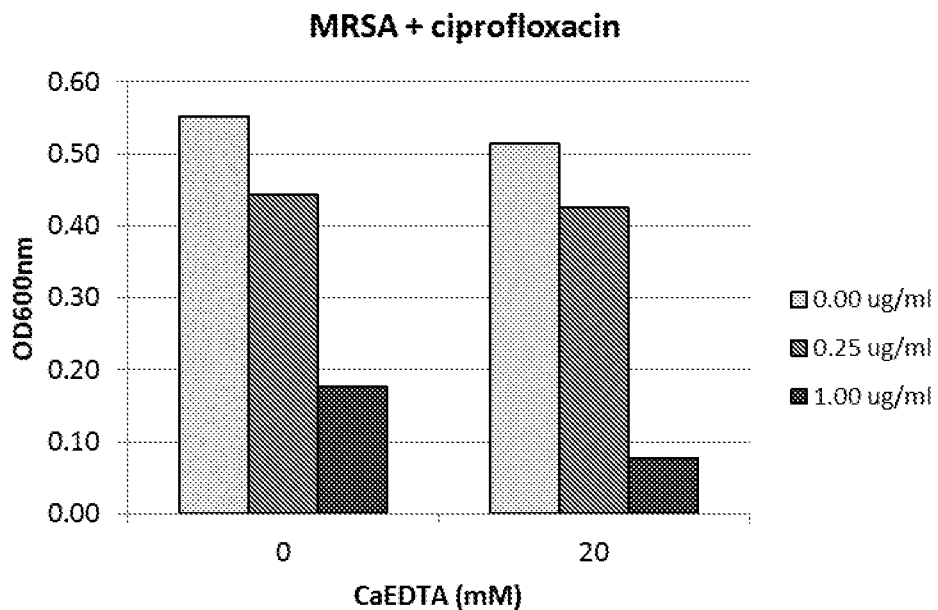
FIG. 21A: Checkerboard assay.
Figure 21B:
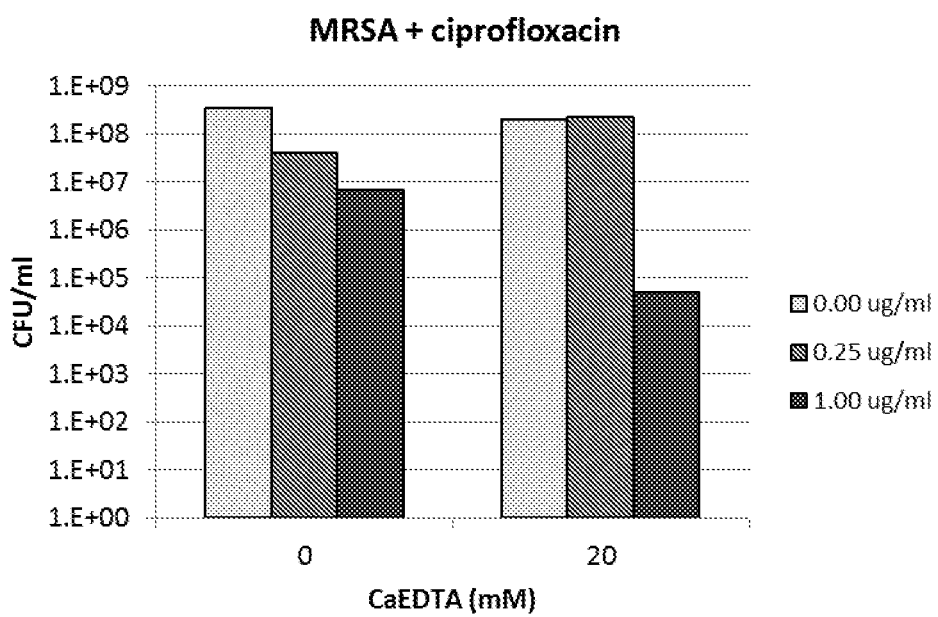
FIG. 21B: Colony counts of selected concentrations.
Figure 22:
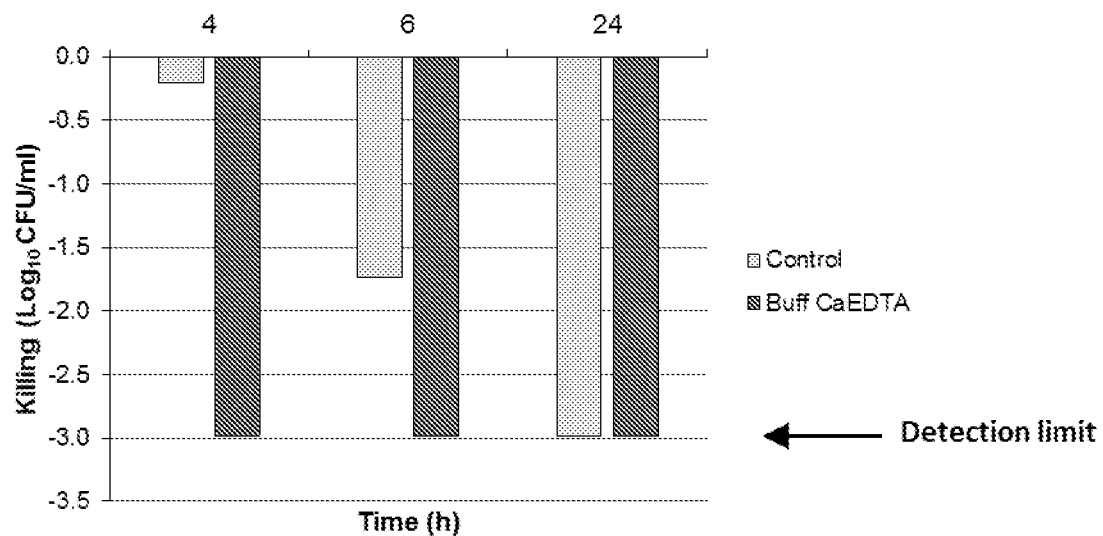
FIGS. 22-23 demonstrate that CaEDTA increases the bactericidal activity of antibiotics.
Figure 23:
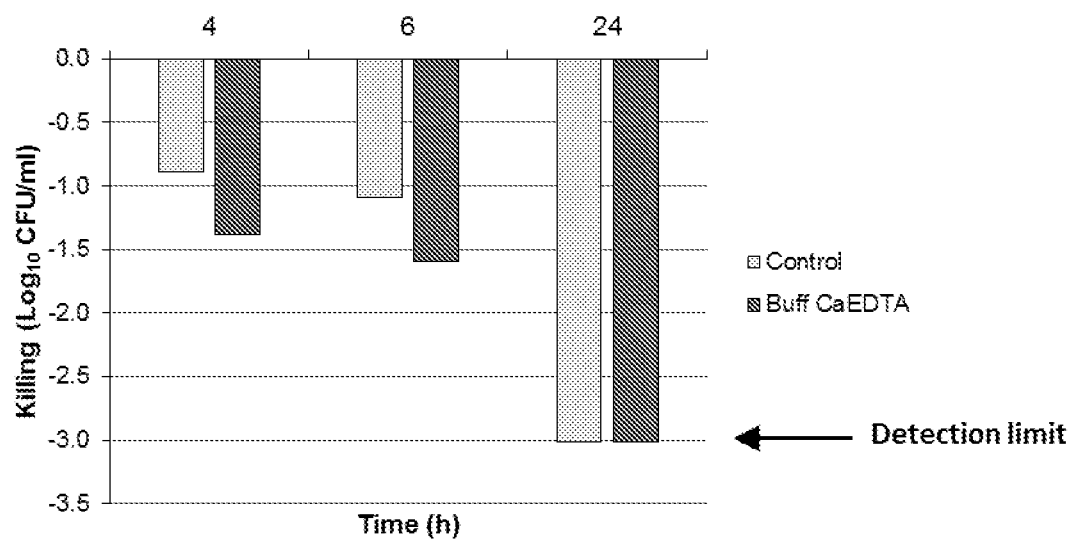

FIG. 21 shows that the killing of *P. aeruginosa* by ceftazidime is much more rapid in the presence of buffered CaEDTA. FIG. 22 shows a similar effect for meropenem against *B. cepacia*.

Example 6: A High Concentration of Nebulised or Dry Powder Chelating Agent Enhances the Killing of Tobramycin on *P. aeruginosa* Biofilms Grown in Realistic Conditions Formulations for inhaled treatments include nebulizing solutions and dry powders. A CaEDTA dry powder was prepared by dry milling to produce submicron-size particles that can be dispersed by standard delivery devices.

Biofilms were grown in a realistic in vitro model using suspended drops of cystic fibrosis mucus harvested from epithelial cell lines (Haley, C. L., Colmer-Hamood, J. A., and Hamood, A. N. (2012). Characterization of biofilm-like structures formed by *Pseudomonas aeruginosa* in a synthetic mucus medium. BMC Microbiol 12, 181.). Cultures of a *P. aeruginosa* clinical strain (MIC tobramycin>256 µg/ml) were grown into late stationary phase in M63 with no carbon source to mimic nutrient limitation.

Drops of mucus (5 µl) were suspended from an inverted IBIDI cover slip and inoculated with $10^3$ cfu, then incubated in a humidified environment at 35° C. for 72 hours to allow biofilm development. Drops were then treated for 5 min with either nebulised tobramycin (20 mg/ml), aerosolised EDTA particles (10 mg/ml), or both. Controls were treated with a 50/50 solution of nebulised 0.9% saline/water. Following treatment, the drops were incubated for 16 hours, then stained with BacLight LIVE/DEAD (1 µl), and fixed in paraformaldehyde vapour for 30 min. Biofilms were visualised using confocal microscopy.

Figure 24A:
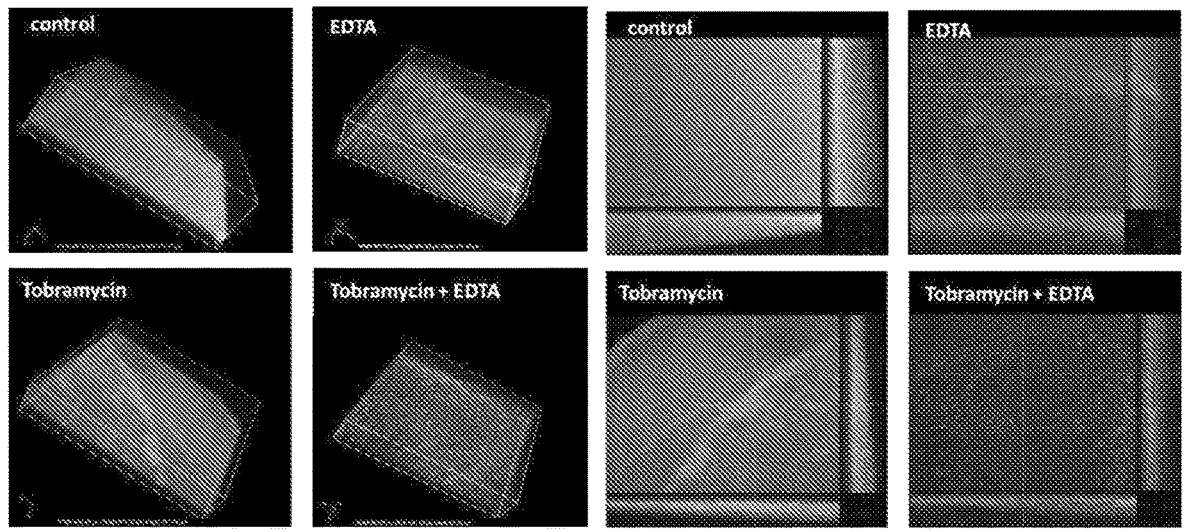
FIG. 24A: Confocal microscopy images of biofilms stained with BacLight LIVE/DEAD.
Figure 24B:
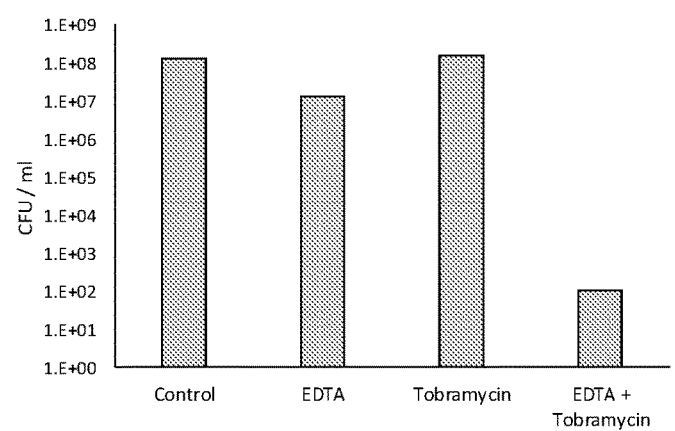
FIG. 24B: Bacterial counts showing the quantitative effect of treatments.

FIG. 24A shows thick and robust biofilms with mostly live cells (green) after treatment with nebulised saline. As expected with a resistant strain, tobramycin treatment alone has little effect on viability. CaEDTA alone causes some degree of killing (red cells). Strikingly, a combination of tobramycin and CaEDTA kills the vast majority of biofilm cells. FIG. 241B shows a quantitative representation of the microscopy images in FIG. 24A. Control biofilms were $1 \times 10^8$ colony forming units (CFU)/ml, while EDTA-to-bramycin treated biofilms were reduced by >6 orders of magnitude to $<10^2$ CFU/ml.

Aminoglycoside antibiotics have a low therapeutic index, meaning there is a narrow window between therapeutic and toxic effects, which in the case of tobramycin include nephrotoxicity and ototoxicity. Drug delivery directly to the lungs to achieve high peak concentrations can also be challenging, especially in patients with reduced lung function. This often leads to treatment with sub-inhibitory antibiotic concentrations, which selects for resistant strains of the infecting bacteria.

Example 7: A High Dose of Inhaled Chelating Agent Reduces *P. aeruginosa* Infection in CF Lungs Patients with CF aged years admitted to hospital with an exacerbation were randomised to receive EDTA or saline (placebo) in addition to their usual treatment of intravenous antibiotics and nebulised tobramycin. EDTA was administered together with tobramycin as a nebulised solution of 4 ml 50 mM CaNa$_2$EDTA, 111 mM Tris in 0.9% saline, pH 7.1. Following randomisation, subjects were treated in hospital for two weeks during which they received the treatment four times a day (300 mg EDTA/day, or up to 3.3 mg EDTA/kg/day). Patients were then discharged and treatment was continued twice a day for four weeks. Patients were monitored for a further four weeks, bringing the total study time to 10 weeks.

Sputum was induced with nebulised 3% hypertonic saline at 8-10 L/min for minutes. Samples were collected prior to treatment, and at 2, 6 and 10 weeks, processed according to the relevant protocol and stored at −80° C. Mucus was dissected from the clear sputum mixed with Sputalysin (1 ml per gram sputum), vortexed and incubated for an hour, then placed into Skim Milk Glycerol storage medium and stored at −80° C.

Samples were thawed on ice, serial dilutions were made to a maximum of 10-7 from original concentration, and 204 of each dilution placed onto each of three culture plates of McConkey agar for *Pseudomonas* spp. Plates were incubated at 35° C. for 48 hours and bacteria were enumerated by colony counts. *P. aeruginosa* identification was further confirmed by Gram stain (negative), oxidase test (negative) and resistance to C390 antibiotic. Data was expressed as colony forming units per millilitre (CFU/ml).

Figure 25:
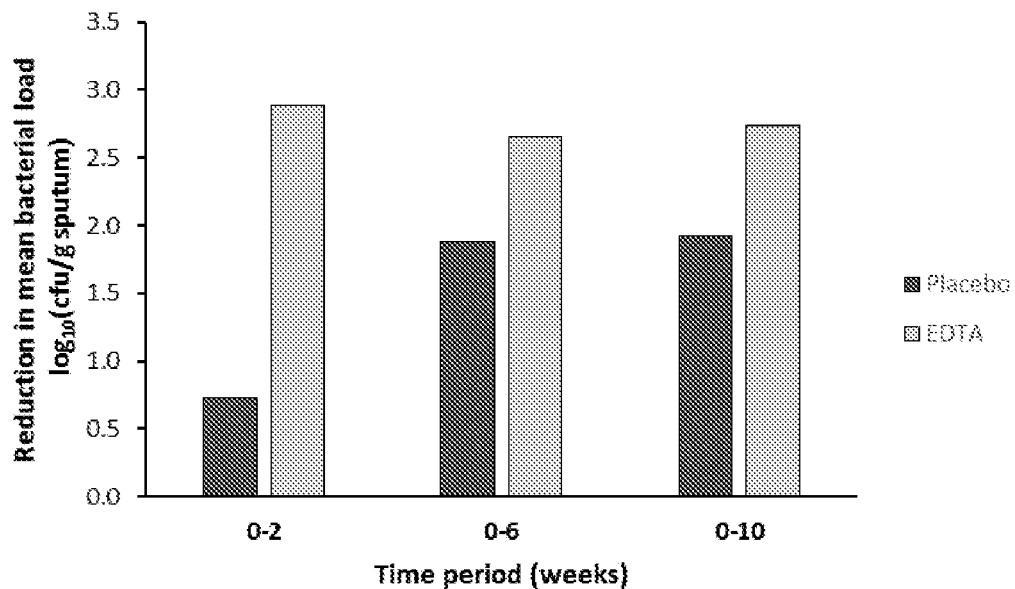
FIGS. 25-28 demonstrate that treatment of CF subjects with buffered CaEDTA in addition to tobramycin is more effective than treatment with tobramycin alone.

FIG. 25 shows the change in colony counts for *P. aerugionsa* (McC) at 2 and 6 weeks compared to the start of treatment. After two weeks of treatment, the reduction in colony counts was >400-fold in the EDTA group compared with 4.5-fold in the placebo group.

Example 8: A High Dose of Inhaled Chelating Agent Results in a Concentration-Dependent Increase in FEV1

Patients with CF aged ≥6 years admitted to hospital with an exacerbation were randomised to receive EDTA or saline (placebo) in addition to their usual treatment of intravenous antibiotics and nebulised tobramycin. EDTA was administered together with tobramycin as a nebulised solution of 4 ml 50 mM CaEDTA, 111 mM Tris in 0.9% saline, pH 7.1. Following randomisation, subjects were treated in hospital for two weeks during which they received the treatment four times a day (300 mg EDTA/day, or up to 3.3 mg EDTA/kg/day). Subjects were then discharged and treatment was continued twice a day for four weeks. Patients were monitored for a further four weeks, bringing the total study time to 10 weeks. At each study visit, lung function was measured by spirometry. Data was recorded as the best of three attempts, and results were expressed as % predicted.

Figure 26:
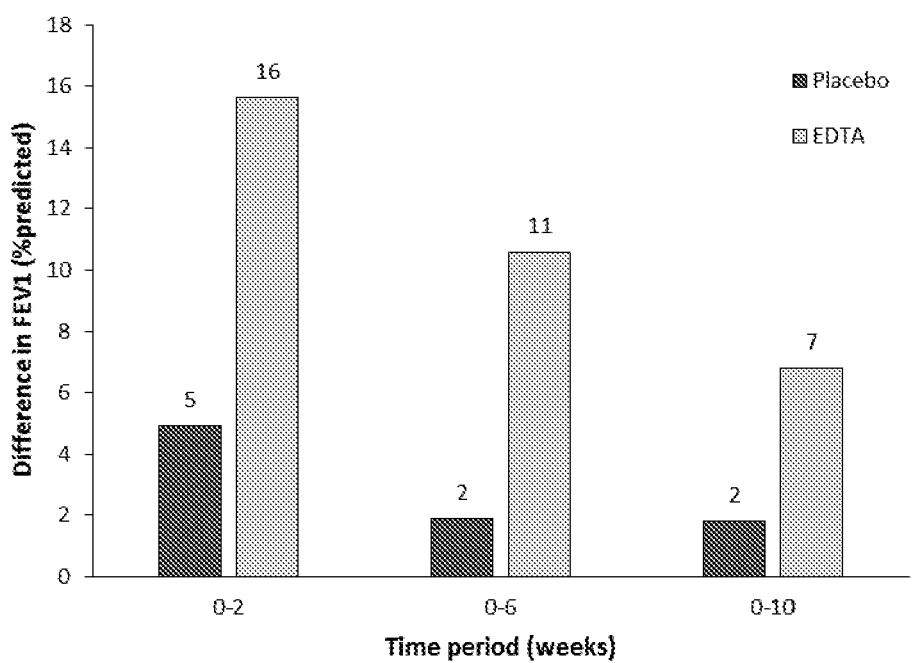

FIG. 26 shows the mean change in FEV1 for both groups at 2, 6 and 10 weeks after the start of the treatment. This demonstrates a clear improvement in lung function in the EDTA group, but little change in the placebo group.

Figure 27:
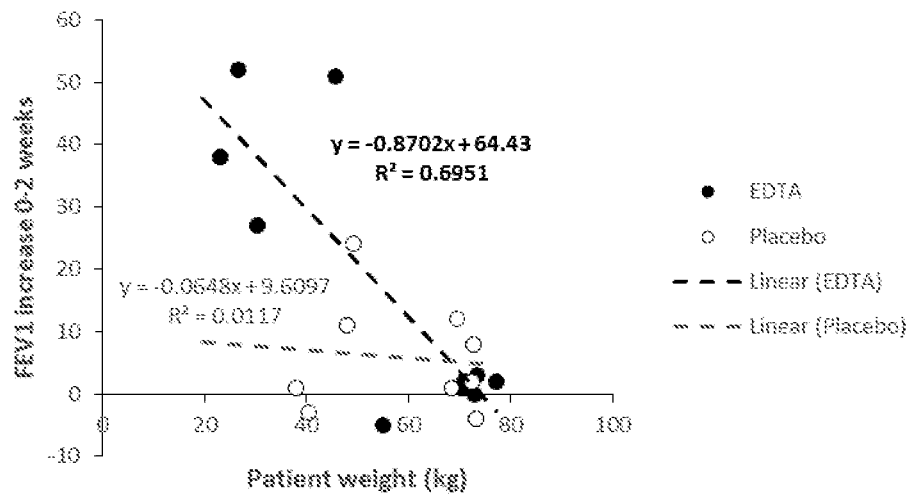

FIG. 27 shows an inverse correlation between FEV1 improvement and body weight in the EDTA group ($R^2=0.70$), but no correlation in the placebo group treated with tobramycin alone ($R^2=0.01$). This shows that EDTA has a dose-dependent effect on lung function (mg EDTA/kg body weight).

The concentration of EDTA achieved in expectorated sputum was measured by LC-MS/MS. To confirm that EDTA penetrates CF mucus to reach the bacteria that are most difficult to treat, mucus plugs were dissected out from the sputum, and a known mass was placed into a smoked glass HPLC vial. LC-MS grade methanol (1 ml) containing $3-C^{13}$ labelled EDTA (10 µM) was added to each vial, mixed by vortexing for 5 minutes and chilled for 20 min at $-20°$ C. Vials were then centrifuged at 100 g for 5 min to sediment precipitated proteins and 754 µL of the methanol extract taken for derivatisation. Concentrated hydrochloric acid (246 µl) added, vials were vortex mixed and incubated at 65° C. for 6 hours to methyl esterify the EDTA. Derivatised extract (1 µl) was injected into a Waters microflow HPLC equipped with a triple quad mass spectrophotometer detector. At a fragmentation energy of 135.0V, the counts of quantification ions of m/z 190.1 for the labelled EDTA and m/z 188.0 for the unlabelled EDTA were used to quantify the amount of extracted derivatised EDTA present in the sample.

Figure 28:
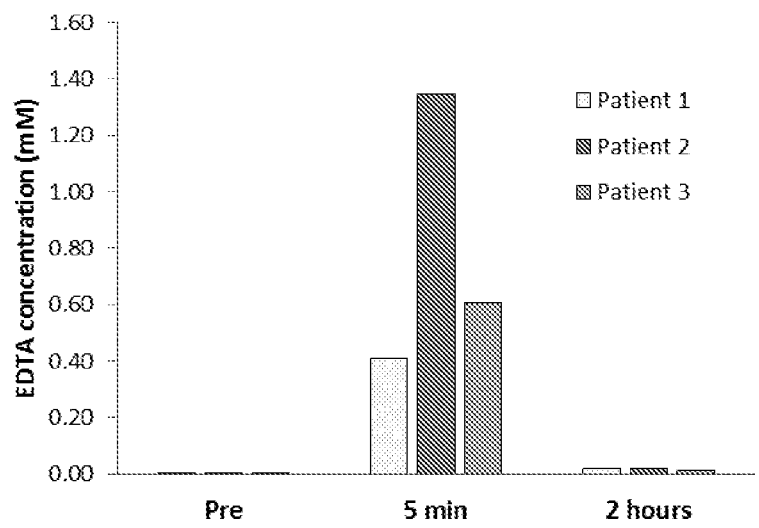

FIG. 28 shows that the EDTA concentration in mucus plugs 5 minutes after treatment is in the millimolar range. This demonstrates efficient delivery and good penetrations through mucus. Peak concentrations in the airway surface liquid are likely higher. EDTA was still detectable in mucus after two hours albeit at much lower levels, likely due to a combination of distribution and clearance.

Prophetic Example P1: Chelators Act in Synergy with Antibiotics to Enhance Antibiotic Efficacy A method to test synergy between antibiotics and chelators is the checkerboard method. A range of different bacterial species are grown to biofilms in 96-well plates, then challenged with varying concentrations of chelators and antibiotics. Colorimetric tests are used to show biofilm levels and metabolic activity (Bueno "Anti-Biofilm Drug Susceptibility Testing Methods: Looking for New Strategies against Resistance Mechanism J Microbial Biochem Technol 2014, S3; Orhan et al., "Synergy tests by E test and checkerboard methods of antimicrobial combinations against *Brucella melitensis*". J Clin Microbiol. 2005 January; 43(1):140-3).

It would be expected that this experiment would show a concentration-dependent reduction in biofilms with increased concentrations of each of antibiotics or chelators alone, and further reduced biofilm levels with a combination of both.

Prophetic Example P2: Buffering Enhances the Ability of Chelators to Accentuate Biofilm Killing by Antibiotics A range of different bacterial species are grown to biofilms in 96-well plates, then challenged with varying concentrations of chelators and buffering agents, such as Tris. Colorimetric tests are used to show biofilm levels and metabolic activity. Bacterial biofilms are further challenged with chelators and antibiotics while varying the acidity of the environment.

Aminoglycoside antibiotics are known to work better against planktonic cells and biofilms in vitro and in vivo at high pH (Lebeaux et al., J Infect Dis. 2014 210(9):1357-66), and the affinity of chelators like EDTA increases with pH. It would therefore be expected that this experiment would show that the efficacy of chelators as antibiotic adjuvants is highest at physiological pH or above.

Prophetic Example P3: In Vivo Study of the Effect of High Dose of Nebulised Chelating Agent on Inflammation, Lung Damage, and Oxidative Stress Subjects with CF aged years admitted to hospital with an exacerbation are randomised to receive nebulised EDTA or saline (placebo) in addition to their usual treatment of intravenous antibiotics and nebulised tobramycin. EDTA is administered together with tobramycin as a nebulised solution of 4 ml 50 mM CaEDTA, 111 mM Tris in 0.9% saline, pH 7.1.

Following randomisation, subjects are treated in hospital for two weeks during which they receive the treatment four times a day (300 mg EDTA/day, or up to 3.3 mg EDTA/kg/day). Subjects are then discharged and treatment continued twice a day for four weeks. Subjects are monitored for a further four weeks, bringing the total study time to 10 weeks. Sputum is collected by induction with nebulised 3% hypertonic saline at 8-10 L/min for minutes. Samples are collected prior to treatment, and at 2, 6 and 10 weeks, processed according to the relevant protocol and stored at −80° C.

Inflammatory Marker Expression

Expectorated sputum is stored in RNAlater®, total RNA is extracted using a Qiagen RNEasy® or similar extraction kit, converted into cDNA, and inflammatory markers are monitored using qPCR as described by Sivaneson et al. (Sivaneson, M., Mikkelsen, H., Ventre, I., Bordi, C., and Filloux, A. (2011). Two-component regulatory systems in *Pseudomonas aeruginosa*: an intricate network mediating fimbrial and efflux pump gene expression. Mol Microbiol 79, 1353-1366) and quantified relative to known housekeeping genes, such as actin and/or GAPDH.

It would be expected that this experiment would show a mean reduction in the gene expression of inflammatory markers in the EDTA group compared with the placebo group.

Cell Damage, Free Iron and Oxidative Stress

Expectorated sputum is frozen directly without processing and assayed for inflammatory markers as above. As a measure of structural damage, levels of matrix metalloproteinases (MMPs) and tissue inhibitors of metalloproteinases (TIMPs) are measured using gelatin zymography and immunoassays, respectively, as previously described (Gaggar et al., *Eur Respir J.* 2011 38(3): 721-727; Garratt et al., *Eur*

Respir J. 2015 46(2):384-94). The amount of iron in the sputum is quantified by ICP-MS as previously described (Hunter et al., *MBio*. 2013 4(4):1-8). The amount of iron-binding proteins is assessed using immunoassays. Oxidative stress is assessed by measuring glutathione (GSSG and GSH) using immunoassays as previously described (Kettle et al., *Eur Respir J.* 2014 44(1):122-9).

It would be expected that this experiment would show a reduction in inflammatory markers in the EDTA group compared with the placebo group. It would be further expected that this experiment would show a change in the balance between MMPs and TIMPs, especially MMP-9 and TIMP-1, which are associated with progression of bronchiectasis.

Prophetic Example P4: In Vivo Study of the Effect of a High Dose of Dry Powder Chelating Agent on Infection, Inflammation, and Oxidative Stress Subjects with CF who need treatment with dry powder tobramycin are allocated into four cohorts and receive 112 mg dry powder twice a day for 28 days. In addition, Cohort 1 (patients>18 years) receives ascending doses of dry powder CaEDTA (37.5 mg BID for 1 week; 75 mg BID for 2 weeks, 150 mg BID for 1 week). Patients in cohort 2 (>18 years) receive CaEDTA (37.5 mg BID for 1 week; 75 BID for 2 weeks; 75 mg QID for 1 week). Patients in cohort 3 (12-18 years) receive CaEDTA (37.5 mg BID for 1 week; 75 mg BID for 2 weeks, 150 mg BID for 1 week. Finally, a control cohort receives tobramycin alone for 28 days.

Sputum samples are collected weekly and assessed for markers of infection and inflammation. Bacteria are monitored by sputum colony counts. As a measure of structural damage, levels of matrix metalloproteinases (MMPs) and tissue inhibitors of metalloproteinases (TIMPs) are measured using gelatin zymography and immunoassays, respectively, as previously described (Gaggar et al., *Eur Respir J.* 2011 38(3): 721-727; Garratt et al., *Eur Respir J.* 2015 46(2):384-94). The amount of iron in the sputum is quantified by ICP-MS as previously described (Hunter et al., 2013). The amount of iron-binding proteins is assessed using immunoassays. Myeloperoxidase activity is also assayed as a measure of neutrophilic inflammation as previously described (Gaggar et al., 2011). 3-chlorotyrosine is measured as a biomarker of the potent oxidant hypochlorous acid. Levels are measured using stable isotope dilution gas chromatography with mass spectrometry (Gaggar et al., 2011). Protein carbonyls are measured as an indicator of reactive oxygen species (ROS) using a commercial immunoassay kit (Gaggar et al., 2011). Oxidative stress is assessed by measuring glutathione (GSSG and GSH) using immunoassays as previously described (Kettle et al., 2014). Gene expression of inflammatory and oxidative stress markers (e.g. IL-8, IL-6, TNFa) will also be monitored by Nanostring, and proteins will be measured by ELISA. Oxidative stress can also be measured via metabolites, such as molondialdehyde (colorimetric assay) or 8-isoprostane (ELISA). Iron will be measured by elemental analysis using laser ablation-inductively coupled plasma-mass spectrometry (LA-ICP-MS).

It would be expected that this experiment would show a reduction in inflammatory markers in the EDTA group compared with the placebo group, and a decrease in iron levels. It would be further expected that this experiment would show a change in the balance between MMPs and TIMPs, especially MMP-9 and TIMP-1, which are associated with progression of bronchiectasis.

It would be further expected that the experiment would show a reduction of bacterial load in sputum and an increase in FEV1 in subjects treated with EDTA compared with control patients.

Prophetic Example P5: In Vivo Study of the Effect of High Dose of Dry Powder Chelating Agent on Inflammation, Lung Damage, and Oxidative Stress Subjects with CF aged years admitted to hospital with an exacerbation are randomised to receive dry powder EDTA or saline (placebo) in addition to their usual treatment of intravenous antibiotics and nebulised tobramycin. EDTA is administered together with tobramycin as a nebulised solution of 4 ml 50 mM CaEDTA, 111 mM Tris in 0.9% saline, pH 7.1.

Following randomisation, subjects are treated in hospital for two weeks during which they receive the treatment four times a day (300 mg EDTA/day, or up to 3.3 mg EDTA/kg/day). Subjects are then discharged and treatment continued twice a day for four weeks. Subjects are monitored for a further four weeks, bringing the total study time to 10 weeks. Sputum is collected by induction with nebulised 3% hypertonic saline at 8-10 L/min for minutes. Samples are collected prior to treatment, and at 2, 6 and 10 weeks, processed according to the relevant protocol and stored at −80° C.

Inflammatory Marker Expression

Expectorated sputum is stored in RNAlater, total RNA is extracted using a Qiagen RNEasy® or similar extraction kit, converted into cDNA, and inflammatory markers are monitored using qPCR as described by Sivaneson et al. (Sivaneson, M., Mikkelsen, H., Ventre, I., Bordi, C., and Filloux, A. (2011). Two-component regulatory systems in *Pseudomonas aeruginosa*: an intricate network mediating fimbrial and efflux pump gene expression. Mol Microbiol 79, 1353-1366) and quantified relative to known housekeeping genes, such as actin and/or GAPDH.

It would be expected that this experiment would show a mean reduction in the gene expression of inflammatory markers in the EDTA group compared with the placebo group.

Cell Damage, Free Iron and Oxidative Stress

Expectorated sputum is frozen directly without processing and assayed for inflammatory markers as above. As a measure of structural damage, levels of matrix metalloproteinases (MMPs) and tissue inhibitors of metalloproteinases (TIMPs) are measured using gelatin zymography and immunoassays, respectively, as previously described (Gaggar et al., *Eur Respir J.* 2011 38(3): 721-727; Garratt et al., *Eur Respir J.* 2015 46(2):384-94). The amount of iron in the sputum is quantified by ICP-MS as previously described (Hunter et al., *MBio* 2013, 4(4):1-8). The amount of iron-binding proteins is assessed using immunoassays. Oxidative stress is assessed by measuring glutathione (GSSG and GSH) using immunoassays as previously described (Kettle et al., *Eur Respir J.* 2014 44(1):122-9).

It would be expected that this experiment would show a reduction in inflammatory markers in the EDTA group compared with the placebo group, and a decrease in iron levels. It would be further expected that this experiment would show a change in the balance between MMPs and TIMPs, especially MMP-9 and TIMP-1, which are associated with progression of bronchiectasis.

It would be further expected that the experiment would show an increase in FEV1 in subjects treated with EDTA compared with placebo (carrier only).

This is demonstrated in Example 4, above.

Prophetic Example P6: In Vivo Study of the Effect of a High Dose of Chelating Agent on Inflammation, Lung Damage, and Oxidative Stress A single centre, randomised, double blind, crossover study of cystic fibrosis subjects is carried out. Subjects are randomised for treatment with inhaled CaEDTA or saline (placebo) 2-4 times a day for two weeks. This is followed by a washout period and then two weeks of the other treatment (EDTA or placebo).

Iron levels, inflammatory markers, MMP/TIMP and FEV1 are monitored as above. Myeloperoxidase activity are also assayed as a measure of neutrophilic inflammation as previously described (Gaggar et al., 2011). 3-chlorotyrosine is measured as a biomarker of the potent oxidant hypochlorous acid. Levels are measured using stable isotope dilution gas chromatography with mass spectrometry (Gaggar et al., 2011). Protein carbonyls are measured as an indicator of ROS using a commercial immunoassay kit (Gaggar et al., 2011).

It would be expected that this experiment would show reduced levels of iron and inflammatory markers, an altered MMP/TIMP balance, and increased mean FEV1 in subjects treated with EDTA compared with placebo. It would be further expected that this experiment would show reduced myeloperoxidase activity and lower mean levels of chlorotyrosine and carbonyls.

Clinical data demonstrates efficacy (FIG. 25 for reduced bacterial counts; FIG. 26 for improved lung function) at 300 mg/day for two weeks (75 mg QID) and maintenance of effect for a further four weeks at 150 mg/day (75 mg BID). Given the significant magnitude of the improvement (average 16% points), as would be understood by persons skilled in the art, it is highly likely that much lower doses are effective, i.e. 75 mg/day (37.5 mg BID), as envisaged by Prophetic Example P4.

FIG. 28 shows that a single dose of 75 mg CaEDTA results in up to 1.34 mM EDTA inside mucus plugs after 30 minutes. The concentration in the airway surface liquid is therefore most likely substantially higher. In vitro data (FIGS. 1B and 2B) demonstrate that CaEDTA is effective at concentrations as low as 0.078 mM EDTA, or 17 times lower than the sputum concentration. As such, it would be reasonable to expect that a daily dose of 37.5 (4-fold lower than the lower dose with clinical benefits) would show efficacy in a fully powered study. This would especially be the case in younger patients who receive a higher dose per body weight and generally show a greater response in FEV1 (FIG. 27).

Numerous variations and modifications of the above-described modes of carrying out the various embodiments of this invention will be apparent to those skilled in the art, based on the above teachings related to the disclosed invention, without departing from the basic inventive concepts. The above embodiments of the invention are merely exemplary and should not be construed to be in any way limiting and all such variations and modifications are to be considered within the scope of the present invention, the nature of which is to be determined from the foregoing description.

Work on this invention was supported by awards from Cystic Fibrosis Foundation Therapeutics

The invention claimed is:

1. A method of treating a bacterial infection in the lung of a subject by administering from 10 mg/day to 2,000 mg/day of an inhaled antibiotic, and from 37.5 mg/day to 1,200 mg/day of an inhaled chelating agent, each in one or more doses, wherein the one or more doses of each of the chelating agent and/or the antibiotic is administered over a period of no more than 2 h and in the absence of acidified nitrite, and wherein the chelating agent is administered at a concentration of at least 50 mM.

2. The method of claim 1 wherein the chelating agent is CaEDTA.

3. The method of claim 1 wherein the antibiotic is an aminoglycoside antibiotic, a beta lactam antibiotic, a glycopeptide antibiotic, colistin, aztreonam or ciprofloxacin.

4. The method of claim 3 wherein the aminoglycoside antibiotic is tobramycin.

5. The method of claim 1 wherein the treatment of infection results in:
   i) an increase in FEV;
   ii) a reduction in inflammation;
   iii) a reduction in MMP activity; and/or
   iv) a reduction in the production of hydroxyl radicals.

6. The method of claim 1 wherein the chelating agent is combined with tris(hydroxymethyl)aminomethane (TRIS).

7. The method of claim 1 wherein:
   i) the chelating agent is administered between one and four times daily; and/or
   ii) the antibiotic is administered between one and four times daily.

8. A kit for treating a bacterial infection in the lung of a subject, wherein said kit contains:
   (a) (i) at least 37.5 mg of an inhaled chelating agent; and (ii) instructions for use, wherein the instructions provide that from 37.5 mg/day to 1,200 mg/day of the inhaled chelating agent is delivered with from 10 mg/day to 2,000 mg/day of an inhaled antibiotic, wherein the one or more doses of each of the chelating agent and/or antibiotic is administered over a period of no more than 2 h; or
   (b) (i) an inhaled antibiotic; and (ii) instructions for use, wherein the instructions provide that from 10 mg/day to 2,000 mg/day of the antibiotic is delivered with from 37.5 mg/day to 1,200 mg/day of an inhaled chelating agent, wherein the one or more doses of each of the chelating agent and/or antibiotic is administered over a period of no more than 2 h; or
   (c) (i) at least 37.5 mg of an inhaled chelating agent and an inhaled antibiotic; and (ii) instructions for use, wherein the instructions provide that from 37.5 mg/day to 1,200 mg/day of the inhaled chelating agent and from 10 mg/day to 2,000 mg/day of the antibiotic are delivered, wherein the one or more doses of each of the chelating agent and/or antibiotic is administered over a period of no more than 2 h;
   wherein the inhaled chelating agent is at a concentration of at least 50 mM and the kit does not comprise acidified nitrite.

9. A composition comprising:
   from 37.5 mg/day to 1,200 mg/day of an inhaled chelating agent and from 10 mg/day to 2,000 mg/day of an inhaled antibiotic for the treatment of infection, wherein the inhaled chelating agent is at a concentration of at least 50 mM, and wherein the composition does not comprise acidified nitrite.

10. The method of claim 1 wherein the one or more doses of each of the chelating agent and/or the antibiotic is administered over a period of no more than 1 hour.

11. The method of claim 1 wherein the one or more doses of each of the chelating agent and/or the antibiotic is administered over a period of no more than 30 minutes.

12. The method of claim 1 wherein the one or more doses of each of the chelating agent and/or the antibiotic is administered over a period of no more than 15 minutes.

13. The method of claim 1 wherein the one or more doses of each of the chelating agent and/or the antibiotic is administered over a period of no more than 5 minutes.

* * * * *